US012734237B2

(12) United States Patent
Cao et al.

(10) Patent No.: US 12,734,237 B2
(45) Date of Patent: Sep. 15, 2026

(54) FORMULATION COMPRISING ANTI-IL-23P19 ANTIBODY, METHOD FOR PREPARING SAME AND USE THEREOF

(71) Applicant: INNOVENT BIOLOGICS (SUZHOU) CO., LTD., Suzhou (CN)

(72) Inventors: Wei Cao, Suzhou (CN); Liqiang Ma, Suzhou (CN); Yinjue Wang, Suzhou (CN); Kaisong Zhou, Suzhou (CN)

(73) Assignee: INNOVENT BIOLOGICS (SUZHOU) CO., LTD., Suzhou (CN)

( * ) Notice: Subject to any disclaimer, the term of this patent is extended or adjusted under 35 U.S.C. 154(b) by 759 days.

(21) Appl. No.: 17/924,214

(22) PCT Filed: May 12, 2021

(86) PCT No.: PCT/CN2021/093219
§ 371 (c)(1),
(2) Date: Nov. 9, 2022

(87) PCT Pub. No.: WO2021/228113
PCT Pub. Date: Nov. 18, 2021

(65) Prior Publication Data

US 2023/0173069 A1 Jun. 8, 2023

(30) Foreign Application Priority Data

May 13, 2020 (CN) ......................... 202010404834.4

(51) Int. Cl.
*A61K 39/395* (2006.01)
*A61K 47/22* (2006.01)
*A61K 47/26* (2006.01)
*C07K 16/24* (2006.01)

(52) U.S. Cl.
CPC ........ *A61K 39/39591* (2013.01); *A61K 47/22* (2013.01); *A61K 47/26* (2013.01); *C07K 16/244* (2013.01)

(58) Field of Classification Search
CPC .. A61K 39/39591; A61K 47/22; A61K 47/26; A61K 9/19; A61K 47/183; A61K 9/0019; A61K 9/08; A61K 47/12; A61K 2039/505; C07K 16/244; C07K 16/24; A61P 37/00; A61P 29/00
See application file for complete search history.

(56) References Cited

U.S. PATENT DOCUMENTS 6,171,586 B1 1/2001 Lam et al.
7,083,784 B2 8/2006 Dall'Acqua et al.
7,491,391 B2 2/2009 Benson et al.
7,658,921 B2 2/2010 Dall'Acqua et al.
7,670,600 B2 3/2010 Dall'Acqua et al.
7,704,497 B2 4/2010 Dall'Acqua et al.
8,012,476 B2 9/2011 Dall'Acqua et al.
8,323,962 B2 12/2012 Dall'Acqua et al.
8,475,792 B2 7/2013 Dall'Acqua et al.
8,513,389 B2 8/2013 Presta et al.
8,795,661 B2 8/2014 Dall'Acqua et al.
9,562,100 B2 2/2017 Dall'Acqua et al.
9,718,884 B2 8/2017 Millican, Jr. et al.
2007/0009526 A1 1/2007 Benson et al.
2010/0111966 A1 5/2010 Presta et al.
2011/0311527 A1 12/2011 Stern et al.
2013/0315911 A1 11/2013 Stevens et al.
2014/0079714 A1 3/2014 Valdes et al.
2014/0086931 A1 3/2014 Krause et al.
2014/0178401 A1 6/2014 Nabozny et al.
2015/0329632 A1 11/2015 Kashi et al.
2016/0237151 A1 8/2016 Benson et al.
2018/0008707 A1 1/2018 Bussemer et al.
2018/0105588 A1 4/2018 Baum et al.
2018/0134784 A1 5/2018 Fitzgerald et al.
2021/0115130 A1 4/2021 Liu et al.
2021/0188961 A1 6/2021 Huang et al.
2022/0064280 A1 3/2022 Friedrich et al.
2022/0073603 A1 3/2022 Hsu et al.
2023/0159633 A1 5/2023 Germinaro et al.
2023/0173069 A1 6/2023 Cao et al.

FOREIGN PATENT DOCUMENTS

CN 101252951 A 8/2008
CN 101389351 A 3/2009
CN 101663320 A 3/2010
CN 101687925 A 3/2010
CN 102202655 B 9/2011
CN 102887954 B 2/2015
CN 104507497 A 4/2015
CN 104870016 A 8/2015
CN 107206081 A 9/2017
CN 107635581 A 1/2018

(Continued)

OTHER PUBLICATIONS

Singh et al: Selective targeting of the IL23 pathway: Generation and characterization of a novel high-affinity humanized anti-IL23A antibody; mAbs, 2015, 7:4, 778-791.
Oppmann, et al. "Novel p19 Protein Engages IL-12p40 to Form a Cytokine, IL-23, with Biological Activities Similar as Well as Distinct from IL-12", (2000) Immunity, 13:715-725.
Wiekowski, et al. "Ubiquitous Transgenic Expression of the IL-23 Subunit p19 Induces Multiorgan Inflammation, Runting, Infertility, and Premature Death", (2001) J. Immunol. 166:7563-7570.

(Continued)

*Primary Examiner* — Stacey N Macfarlane
(74) *Attorney, Agent, or Firm* — LEASON ELLIS LLP

(57) ABSTRACT

The present invention relates to a formulation comprising an anti-IL-23p19 antibody, and in particular to a pharmaceutical formulation comprising an anti-IL-23p19 antibody, a buffer, a stabilizer and a surfactant. Furthermore, the present invention further relates to therapeutic or prophylactic use of these formulations.

23 Claims, 2 Drawing Sheets

Specification includes a Sequence Listing.

(56) References Cited

FOREIGN PATENT DOCUMENTS

| | | | |
|---|---|---|---|
| CN | 108026168 | A | 5/2018 |
| CN | 108064249 | A | 5/2018 |
| CN | 109206516 | A | 1/2019 |
| CN | 111936165 | A | 11/2020 |
| CN | 112638420 | A | 4/2021 |
| CN | 113825768 | A | 12/2021 |
| CN | 112334483 | B | 5/2022 |
| EP | 1355919 | B1 | 11/2010 |
| EP | 2341060 | A1 | 7/2011 |
| EP | 2354149 | A1 | 8/2011 |
| EP | 3326649 | A1 | 5/2018 |
| IN | 103396489 | A | 11/2013 |
| JP | 2009501006 | A | 1/2009 |
| JP | 2009523012 | A | 6/2009 |
| JP | 2010-518856 | | 6/2010 |
| JP | 2016505572 | A | 2/2016 |
| JP | 7517999 | | 7/2024 |
| TW | 1779253 | B | 10/2022 |
| TW | 1802882 | B | 5/2023 |
| WO | 2006/044908 | A2 | 4/2006 |
| WO | 2006/050166 | A2 | 5/2006 |
| WO | 2007/005955 | A2 | 1/2007 |
| WO | 2007/075624 | A1 | 7/2007 |
| WO | 2007/076524 | A2 | 7/2007 |
| WO | 2008/103432 | A1 | 8/2008 |
| WO | 2008/103473 | A1 | 8/2008 |
| WO | 2010/027766 | A1 | 3/2010 |
| WO | 2011032148 | A1 | 3/2011 |
| WO | 2011/161226 | A2 | 12/2011 |
| WO | 2013/165791 | A1 | 11/2013 |
| WO | 2018/093841 | A1 | 5/2018 |
| WO | 2020055651 | A1 | 3/2020 |
| WO | 2020108530 | A1 | 6/2020 |
| WO | 2021228113 | A1 | 11/2021 |
| WO | 2022190034 | A1 | 9/2022 |
| WO | 2023144699 | A1 | 8/2023 |

OTHER PUBLICATIONS

Parham, et al. "A Receptor for the Heterodimeric Cytokine IL-23 Is Composed of IL-12Rβ1 and a Novel Cytokine Receptor Subunit, IL-23R", (2002) J. Immunol. 168:5699-5708.

Frucht, D. "IL-23: A Cytokine That Acts on Memory T Cells", (2002) Sci STKE 2002, E1-E3.

Elkins, et al. "In Vivo Clearance of an Intracellular Bacterium, Francisella tularensis LVS, Is Dependent on the p40 Subunit of Interleukin-12 (IL-12) but Not on IL-12 p70", (2002) Infection Immunity 70:1936-1948.

Robbie, et al., A Novel Investigational Fc-Modified Humanized Monoclonal Antibody, Motavizumab-YTE, Has an Extended Half-Life in Healthy Adults, Antimicrobial Agents and Chemotherapy, 2013, 57(12): p. 6147-6153.

Cua, et al. "Interleukin-23 rather than interleukin-12 is the critical cytokine for autoimmune inflammation of the brain", (2003) Nature 421:744-748.

Murphy et al. Divergent pro- and antiinflammatory roles for IL-23 and IL-12 in joint autoimmune inflammation. J Exp Med (2003) 198: 1951-1957.

Bravo and Heath, Receptor Recognition by gp130 Cytokines, EMBO J. (2000) 19(11):2399-2411.

Tang, et al., "Interleukin-23: as a drug target for autoimmune inflammatory diseases", Immunology, 135(2), p. 112-124, 2012.

Izcue et al., "Interleukin-23 Restrains Regulatory T Cell Activity to Drive T Cell-Dependent Colitis", Immunity, 28(4), p. 559-570, 2008.

Savvatis et al., "Interleukin-23 Deficiency Leads to Impaired Wound Healing and Adverse Prognosis After Myocardial Infarction", Circulation: Heart Failure, 7(1), pp. 161-171, 2014.

U.S. Appl. No. 61/642,032.

International Search Report and Written Opinion of PCT/CN2019/121261, mailed Mar. 4, 2020.

The State Food and Drug Administration Technical Guidelines for Stability Research of Biological Products, issued on Apr. 15, 2015.

European Medicines Agency, ICH Q1A (R2), Stability Testing of New Drug Substances and Products, Aug. 2003.

International Search Report and Written Opinion of PCT/CN2021/093219, mailed Aug. 16, 2021.

Sheng et al.: "Aberrant expression of IL-23/IL-23R in patients with breast cancer and its clinical significance", Molecular Medicine Reports, 2018, vol. 17, Issue 3: 4639-4644.

Benjamini et al., "Immunology: A Short Course", 1991, 2nd edition, p. 40.

Ferrara et al., "Recombinant renewable polyclonal antibodies", mAbs, 2015, 7(1):32-41.

Al-Lazikani et al, "Standard conformations for the canonical structures of immunoglobulins", Journal of Molecular Biology, 1997, vol. 273, pp. 927-948.

Blauvelt et.al, "Efficacy and safety of guselkumab, an anti-interleukin-23 monoclonal antibody, compared with adalimumab for the continuous treatment of patients with moderate to severe psoriasis: Results from the phase III, double-blinded, placebo- and active comparator-controlled VOYAGE 1 trial", J Am Acad Dermatol. 2017, vol. 76, No. 3, pp. 405-417.

Bravo et al., Receptor recognition by gp130 cytokines', The EMBO Journal, 2000, vol. 19, No. 11, pp. 2399-2411.

Chothia et al., "Conformations of Immunoglobulin hypervariable regions", Nature, 1989, vol. 342, pp. 877-883.

Gordon et al., "Efficacy and safety of risankizumab in moderate-to-severe plaque psoriasis (UltIMMa-1 and UltIMMa-2): results from two double-blind, randomised, placebo-controlled and ustekinumab-controlled phase 3 trials", The Lancet, 2018, 392(10148):650-661. 12 pages.

International Search Report and Written Opinion for PCT/CN2024/090113 mailed Jul. 16, 2024, 26 pages.

International Search Report and Written Opinion for PCT/CN2024/099327 mailed Sep. 10, 2024, 26 pages.

International Search Report and Written Opinion for PCT/CN2024/110996 mailed Oct. 24, 2024, 24 pages.

International Search Report and Written Opinion for PCT/CN2024/117492 mailed Sep. 6, 2024, 21 pages.

Kopp et al., "Clinical improvement in psoriasis with specific targeting of interleukin-23", Nature, 2015. vol. 521, No. 7551, pp. 222-236.

Langley et.al, "Secukinumab in Plaque Psoriasis—Results of Two Phase 3 Trials", The New England Journal of Medicine, 2014, vol. 371, No. 4, pp. 326-338.

Langrish et al., "IL-23 drives a pathogenic T cell population that induces autoimmune inflammation", J Exp Med, 2005, vol. 201, No. 2, pp. 233-240.

Li et al., "IBI112, a Selective Anti-IL23p19 Monoclonal Antibody, Displays High Efficacy in IL-23-induced Psoriasiform dermatitis", International Immunopharmacology, vol. 89, 2020, Article No. 107008, 9 pages.

Menter et al. "Guidelines of care for the management of psoriasis and psoriatic arthritis: Section 1. Overview of psoriasis and guidelines of care for the treatment of psoriasis with biologics", J Am Acad Dermatol, 2008, vol. 58, No. 5, pp. 826-850.

Oppmann et al., "Novel p19 Protein Engages IL-12p40 to Form a Cytokine, IL-23, with Biological Activities Similar as Well as Distinct from IL-12", Immunity, 2000, vol. 13, pp. 715-725.

Reich et.al, "Efficacy and safety of guselkumab, an anti-interleukin-23 monoclonal antibody, compared with adalimumab for the treatment of patients with moderate to severe psoriasis with randomized withdrawal and retreatment: Results from the phase III, double-blind, placebo- and active comparator-controlled VOYAGE 2 trial", J Am Acad Dermatol. 2017, vol. 76, No. 3, pp. 418-431.

Sands et al., "A randomized, double-blind placebo-controlled phase 2a induction study of MEDI2070 (anti-p19 antibody) in patients with active Crohn's disease who have failed anti-TNF antibody therapy", Journal of Crohn's and Colitis, 2015, vol. 9, Sup No. 1, pp. S15-S16.

Sands et al. "Efficacy and Safety of Mirikizumab in a Randomized Phase 2 Study of Patients With Crohn's Disease", Gastroenterology, 2022, vol. 162, No. 2, pp. 495-508.

(56) References Cited

OTHER PUBLICATIONS

Chen et al., "Chinese Experts Consensus on Biologic Therapy for Psoriasis (2019)", Chinese Journal of Dermatology, 2019, vol. 52, No. 12, pp. 863-871, 15 pages.
Zhang et al., "Guidelines for the Diagnosis and Treatment of Psoriasis (2018 Simplified Version)", Chinese Journal of Dermatology, 2019, vol. 52, No. 4, pp. 223-230, 13 pages.
No Author, "Phase I Clinical Study of Single-Dose Administration of IBI112 in Healthy Subjects", Clinical Trial, 2020, 13 pages.
No Author, "Phase II Clinical Study Evaluating the Efficacy and Safety of IBI112 for the Treatment of Moderate-to-Severe Plaque Psoriasis", Clinical Trial, 2021, 16 pages.
No Author, "Phase III Clinical Study Evaluating the Efficacy and Safety of IBI112 for the Treatment of Moderate-to-Severe Plaque Psoriasis, Clinical Trial", 2022, 16 pages.
No Author, "Tremfya® (guselkumab) Prescribing information", 2025, 42 pages.
No Author, "SKYRIZI ® (risankizumab-rzaa) Prescribing Information", 2026, 92 pages.
No Author, "ILUMYA ™ (tildrakizumab-asmn) Precribing Information", 2018, 11 pages.
No Author, "A Study to Evaluate IBI112 in the Treatment of Moderate to Severe Active Ulcerative Colitis", ClinicalTrials, 2023, Trial design, 10 pages.
Friedre et al., "Anti-IL-23 and Anti-IL-17 biologic agents for the treatment of immune mediated inflammatory conditions", Clinical Pharmacology & Therapy, 2018, vol. 103, No. 1, pp. 88-101.
U.S. Appl. No. 19/478,567, filed Oct. 24, 2025, 33 pages.
U.S. Appl. No. 19/510,209, filed Feb. 10, 2026, 45 pages.
U.S. Appl. No. 19/492,754, filed Dec. 12, 2025, 48 pages.
U.S. Appl. No. 19/516,436, filed Mar. 4, 2026, 56 pages.

FORMULATION COMPRISING ANTI-IL-23P19 ANTIBODY, METHOD FOR PREPARING SAME AND USE THEREOF

The present application claims priority to Chinese Patent Application No. 2020104048344 filed on May 13, 2020, the content of which is incorporated herein by reference in its entirety.

TECHNICAL FIELD

The present invention relates to the field of antibody formulations. Particularly, the present invention relates to a pharmaceutical formulation, more particularly a stable liquid formulation, a lyophilized formulation and a reconstituted stable liquid formulation, comprising an anti-IL-23p19 antibody, a method for preparing the pharmaceutical formulation, and therapeutic and/or prophylactic use of the pharmaceutical formulation.

BACKGROUND

Interleukin (IL)-12 is a secreted heterodimeric cytokine consisting of two disulfide-linked glycosylated subunits, which are named p35 and p40 after their approximate molecular weights. It has been found that the p40 subunit of IL-12 can also be linked to an isolated protein subunit named p19 to form a new cytokine, interleukin-23 (IL-23). Interleukin-23 (IL-23) is a heterodimeric cytokine comprising the following two subunits: a p19 specific to IL-23 (IL-23p19) and a p40 shared with IL-12 (IL-12) (IL-12p40). The p19 subunit is structurally related to IL-6, granulocyte colony stimulating factor (G-CSF) and p35 subunit of IL-12. IL-23 mediates signaling by binding to a heterodimeric receptor comprising two subunits, which are IL-23R specific to the IL-23 receptor and IL-12Rb1 shared with the IL-12 receptor.

Many previous studies have demonstrated that the consequences of genetic defects in p40 (p40 knockout mice; p40KO mice) are more serious than those observed in p35-deficient mice (e.g., p35KO mice). These results are generally interpreted as p40 knockout not only blocking IL-12 expression, but also IL-23 expression. See, for example, Oppmann et al. (2000) *Immunity* 13: 715-725; Wiekowski et al. (2001) *J. Immunol.* 166: 7563-7570; Parham et al. (2002) *J. Immunol.* 168: 5699-708; Frucht (2002) *Sci STKE* 2002, E1-E3; and Elkins et al. (2002) *Infection Immunity* 70: 1936-1948. Recent studies have demonstrated that IL-23 inhibition in IL-23p19-deficient mice or by IL-23-specific antibody neutralization can provide benefits comparable to anti-IL-12p40 strategies (Cua et al., 2003; Murphy et al., 2003; Benson et al., 2004). Therefore, increased specificity of IL-23 in immune-mediated diseases is evident. IL-23 neutralization does not inhibit IL-12 pathway and thus can provide effective treatment for immune-mediated diseases, while having limited effect on important host immune defense mechanisms. This will represent a significant improvement over current treatment options. Accordingly, there is a need in the art for a novel IL-23p19 antibody. The IL-23p19 antibody is described, for example, in Patent Application PCT/CN2019/121261.

The stability of a drug is one of key indexes for ensuring the efficacy and safety. A good formulation is a key prerequisite to keep the efficacy and safety of a drug over the shelf life. However, due to the complexity of antibodies and their metabolism pathway, it is currently impossible to predict the formulation conditions required to optimize antibody stability. This is particularly essential considering that different antibodies generally have different CDR sequences, and that such sequence differences will result in different stability properties of the antibodies in a solution. Therefore, based on the stringent requirements for safety and efficacy of antibodies for human use, it is necessary to optimize the formulation for each antibody.

Although some IL-23p19 antibody formulations have been proposed, there remains a need in the art for novel pharmaceutical formulations comprising IL-23p19 antibodies that are sufficiently stable and suitable for administration to human subjects. Furthermore, for such antibody formulations, the simplicity of formulation and ease of use may also be advantageous.

SUMMARY

The present invention satisfies the need described above by providing a pharmaceutical formulation comprising an antibody specifically binding to IL-23p19. The antibody formulation of the present invention has excellent stability under different temperature and time conditions.

Accordingly, in one aspect, the present invention provides a liquid antibody formulation comprising: (i) an anti-IL-23p19 antibody, (ii) a buffer, (iii) a stabilizer, and (iv) a surfactant.

In one embodiment, the anti-IL-23p19 antibody comprises a heavy chain variable region VH and a light chain variable region VL, wherein the heavy chain variable region comprises a sequence of SEQ ID NO: 7 or a sequence having at least 90% identity thereto, and the light chain variable region comprises a sequence of SEQ ID NO: 8 or a sequence having at least 90% identity thereto:

```
sequence
                                          (SEQ ID NO: 7)
QVQLVQSGAEVKKPGASVKVSCKASGYTFTSYLMHWVRQAPGQGLEWMGY

INPYNEGTNYAQKFQGRVTMTRDTSISTAYMELSRLRSDDTAVYYCARNW

DLPYWGQGTLVTVSS;

sequence
                                          (SEQ ID NO: 8)
DIQMTQSPSSLSASVGDRVTITCRASQSISDYLHWYQQKPGKAPKLLIKY

ASQSMSGVPSRFSGSGSGSDFTLTISSLQPEDFATYYCQQGHSFPFTFGQ

GTKLEIK.
```

In one embodiment, the anti-IL-23p19 antibody comprises:

```
a heavy chain VH CDR1 of
                        (SEQ ID NO: 1)
GYTFTSYLMH;

a heavy chain VH CDR2 of
                        (SEQ ID NO: 2)
YINPYNEGTN;

a heavy chain VH CDR3 of
                        (SEQ ID NO: 3)
NWDLPY;

a light chain VL CDR1 of
                        (SEQ ID NO: 4)
RASQSISDYLH;

a light chain VL CDR2 of
                        (SEQ ID NO: 5)
YASQSMS;
```

-continued and a light chain VL CDR3 of (SEQ ID NO: 6) QQGHSFPFT.

In one embodiment, the IL-23p19 antibody is an IgG1 antibody comprising a heavy chain and a light chain, wherein the heavy chain comprises a sequence of SEQ ID NO: 9 or a sequence having at least 90% identity thereto, and wherein the light chain comprises a sequence of SEQ ID NO: 10 or a sequence having at least 90% identity thereto.

```
Sequence
                                        (SEQ ID NO: 9)
QVQLVQSGAEVKKPGASVKVSCKASGYTFTSYLMHWVRQAPGQGLEWMGY

INPYNEGTNYAQKFQGRVTMTRDTSISTAYMELSRLRSDDTAVYYCARNW

DLPYWGQGTLVTVSSASTKGPSVFPLAPSSKSTSGGTAALGCLVKDYFPE

PVTVSWNSGALTSGVHTFPAVLQSSGLYSLSSVVTVPSSSLGTQTYICNV

NHKPSNTKVDKKVEPKSCDKTHTCPPCPAPELLGGPSVFLFPPKPKDTLY

ITREPEVTCVVVDVSHEDPEVKFNWYVDGVEVHNAKTKPREEQYNSTYRV

VSVLTVLHQDWLNGKEYKCKVSNKALPAPIEKTISKAKGQPREPQVYTLP

PSRDELTKNQVSLTCLVKGFYPSDIAVEWESNGQPENNYKTTPPVLDSDG

SFFLYSKLTVDKSRWQQGNVFSCSVMHEALHNHYTQKSLSLSPG

Sequence
                                       (SEQ ID NO: 10)
DIQMTQSPSSLSASVGDRVTITCRASQSISDYLHWYQQKPGKAPKLLIKY

ASQSMSGVPSRFSGSGSGSDFTLTISSLQPEDFATYYCQQGHSFPFTFGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC
```

Preferably, the IL-23p19 antibody is the anti-IL-23p19 antibody 17D1-YTE disclosed in PCT Application No. PCT/CN2019/121261 (International Application Date: Nov. 27, 2019), consisting of the heavy chain sequence of SEQ ID NO: 9 and the light chain sequence of SEQ ID NO: 10.

In one embodiment, the IL-23p19 antibody is recombinantly expressed in HEK 293 cells or CHO cells.

In one embodiment, the IL-23p19 antibody in the liquid antibody formulation disclosed herein is at a concentration of about 1-300 mg/mL. In another embodiment, the IL-23p19 antibody in the liquid antibody formulation disclosed herein is at a concentration of about 25-250 mg/mL, preferably 50-200 mg/mL, e.g., about 50, 60, 70, 80, 90, 100, 110, 120, 130, 140, 150, 160, 170, 180, 190 or 200 mg/mL.

In one embodiment, the buffer in the liquid antibody formulation disclosed herein is selected from a histidine buffer, a citric acid buffer, an acetic acid buffer and a phosphoric acid buffer. Preferably, the buffer is selected from histidine, histidine hydrochloride and a combination thereof. In one embodiment, the histidine buffer is selected from histidine at about 0.775-3.1 mg/mL; preferably, the histidine is at a concentration of about 1.55 mg/mL. In one embodiment, the histidine buffer is a combination of histidine and histidine hydrochloride with a histidine content of about 0.38-1.52 mg/mL and a histidine hydrochloride content of about 0.54-2.16 mg/mL; preferably, the histidine and the histidine hydrochloride are at concentrations of about 0.76 mg/mL and about 1.08 mg/mL, respectively. In one embodiment, the liquid formulation disclosed herein comprises sorbitol as the sole stabilizer. In this embodiment, the amount of sorbitol in the liquid formulation disclosed herein may be about 25-100 mg/mL, e.g., 40-60 mg/mL. For example, sorbitol may be present in an amount of about 40, 42, 44, 46, 48, 50, 52, 54, 56, 58 or 60 mg/mL, preferably about 50 mg/mL.

In one embodiment, the liquid formulation disclosed herein comprises sucrose as the sole stabilizer. In this embodiment, the amount of sucrose in the liquid formulation disclosed herein may be about 40-160 mg/mL, preferably 70-90 mg/mL; for example, sucrose may be present in an amount of about 70, 75, 80, 85 or 90 mg/mL, preferably about 80 mg/mL. In one embodiment, the liquid formulation disclosed herein comprises a combination of sorbitol and arginine as the stabilizer. In the combination, sorbitol may be present in an amount of about 15-60 mg/mL, preferably 20-40 mg/mL, e.g., about 20, 25, 30, 35 or 40 mg/mL. In the combination, arginine may be present in an amount of about 6.97-27.88 mg/mL, preferably 10.45-17.42 mg/mL, particularly about 13.94 mg/mL. Preferably, the liquid formulation disclosed herein comprises sorbitol at about 20-40 mg/mL and arginine at about 10.45-17.42 mg/mL. More preferably, the liquid formulation disclosed herein comprises sorbitol at about 30 mg/mL and arginine at about 13.94 mg/mL.

In one embodiment, the liquid formulation disclosed herein comprises a combination of sucrose and arginine as the stabilizer. In the combination, sucrose may be present in an amount of about 25-100 mg/mL, preferably 40-60 mg/mL, e.g., 40, 42, 44, 46, 48, 50, 52, 54, 56, 58 or 60 mg/mL. In the combination, arginine may be present in an amount of about 6.97-27.88 mg/mL, preferably 10.45-17.42 mg/mL, particularly about 13.94 mg/mL. Preferably, the liquid formulation disclosed herein comprises sucrose at about 40-60 mg/mL and arginine at about 10.45-17.42 mg/mL. More preferably, the liquid formulation disclosed herein comprises sucrose at about 50 mg/mL and arginine at about 13.94 mg/mL.

In one embodiment, the surfactant in the liquid antibody formulation disclosed herein is a non-ionic surfactant. In one embodiment, the surfactant is selected from polysorbate surfactants, poloxamer and polyethylene glycol. In one embodiment, the surfactant is selected from polysorbate surfactants. In one specific embodiment, the surfactant in the liquid antibody formulation disclosed herein is polysorbate 80 or polysorbate 20. In one embodiment, the surfactant in the liquid antibody formulation disclosed herein is at a concentration of about 0.1-1 mg/mL, preferably about 0.2-0.8 mg/mL, e.g., about 0.2, 0.3, 0.4, 0.5, 0.6, 0.7 or 0.8 mg/mL.

In one embodiment, the liquid formulation has a pH of any of 5.2-6.3 (i.e., 5.5±0.3 to 6.0±0.3), e.g., about 5.2, 5.3, 5.4, 5.5, 5.6, 5.7, 5.8, 5.9, 6.0, 6.1, 6.2 or 6.3. Preferably, the formulation has a pH of 6.0±0.3. In one embodiment, the liquid antibody formulation disclosed herein comprises:

(i) an anti-IL-23p19 antibody at about 50-200 mg/mL, e.g., about 50, 100, 150 or 200 mg/mL;

(ii) histidine at about 0.775-3.1 mg/mL;

(iii) sorbitol at about 40-60 mg/mL; and (iv) polysorbate 80 at about 0.2-0.8 mg/mL;

wherein the liquid formulation has a pH of 6.0±0.3, preferably a pH of 6.0;

or the liquid antibody formulation comprises:

(i) an anti-IL-23p19 antibody at about 50-200 mg/mL, e.g., about 50, 100, 150 or 200 mg/mL;

(ii) histidine at about 0.775-3.1 mg/mL;

(iii) sorbitol at about 20-40 mg/mL, and arginine at about 10.45-17.42 mg/mL; and (iv) polysorbate 80 at about 0.2-0.8 mg/mL;

wherein the liquid formulation has a pH of 6.0±0.3, preferably a pH of 6.0;

or the liquid antibody formulation comprises:

(i) an anti-IL-23p19 antibody at about 50-200 mg/mL, e.g., about 50, 100, 150 or 200 mg/mL;

(ii) histidine at about 0.775-3.1 mg/mL;

(iii) sucrose at about 40-60 mg/mL, and arginine at about 10.45-17.42 mg/mL; and (iv) polysorbate 80 at about 0.2-0.8 mg/mL;

wherein the liquid formulation has a pH of 6.0±0.3, preferably a pH of 6.0;

or the liquid antibody formulation comprises:

(i) an anti-IL-23p19 antibody at about 50-200 mg/mL, e.g., about 50, 100, 150 or 200 mg/mL;

(ii) histidine at about 0.775-3.1 mg/mL;

(iii) sucrose at about 70-90 mg/mL; and (iv) polysorbate 80 at about 0.2-0.8 mg/mL;

wherein the liquid formulation has a pH of 6.0±0.3, preferably a pH of 6.0;

or the liquid antibody formulation comprises:

(i) an anti-IL-23p19 antibody at about 50-200 mg/mL, e.g., about 50, 100, 150 or 200 mg/mL;

(ii) histidine at about 0.38-1.52 mg/mL, and histidine hydrochloride at about 0.54-2.16 mg/mL;

(iii) sorbitol at about 40-60 mg/mL; and (iv) polysorbate 80 at about 0.2-0.8 mg/mL;

wherein the liquid formulation has a pH of 6.0±0.3, preferably a pH of 6.0;

or the liquid antibody formulation comprises:

(i) an anti-IL-23p19 antibody at about 50-200 mg/mL, e.g., about 50, 100, 150 or 200 mg/mL;

(ii) histidine at about 0.38-1.52 mg/mL, and histidine hydrochloride at about 0.54-2.16 mg/mL;

(iii) sorbitol at about 20-40 mg/mL, and arginine at about 10.45-17.42 mg/mL; and (iv) polysorbate 80 at about 0.2-0.8 mg/mL;

wherein the liquid formulation has a pH of 6.0±0.3, preferably a pH of 6.0;

or the liquid antibody formulation comprises:

(i) an anti-IL-23p19 antibody at about 50-200 mg/mL, e.g., about 50, 100, 150 or 200 mg/mL;

(ii) histidine at about 0.38-1.52 mg/mL, and histidine hydrochloride at about 0.54-2.16 mg/mL;

(iii) sucrose at about 40-60 mg/mL, and arginine at about 10.45-17.42 mg/mL; and (iv) polysorbate 80 at about 0.2-0.8 mg/mL;

wherein the liquid formulation has a pH of 6.0±0.3, preferably a pH of 6.0;

or the liquid antibody formulation comprises:

(i) an anti-IL-23p19 antibody at about 50-200 mg/mL, e.g., about 50, 100, 150 or 200 mg/mL;

(ii) histidine at about 0.38-1.52 mg/mL, and histidine hydrochloride at about 0.54-2.16 mg/mL;

(iii) sucrose at about 70-90 mg/mL; and (iv) polysorbate 80 at about 0.2-0.8 mg/mL;

wherein the liquid formulation has a pH of 6.0±0.3, preferably a pH of 6.0;

The liquid formulation disclosed herein can be stably stored for a long period of time, e.g., at least 12 months or longer. In one embodiment, the liquid formulation disclosed herein can be stable after storage at about −80° C. to about 45° C., e.g., −80° C., about −40° C., about −30° C., about −20° C., about 0° C., about 5° C., about 25° C., about 35° C., about 38° C., about 40° C., about 42° C., or about 45° C. for at least 10 days, at least 20 days, at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, at least 24 months, at least 36 months, or longer.

In one embodiment, the liquid formulation disclosed herein can be stably stored for at least 12 months. In another embodiment, the liquid formulation disclosed herein is stable at a temperature of at least 40° C. In yet another embodiment, the liquid formulation disclosed herein remains stable at about 2-8° C. for at least 3 months, preferably at least 12 months, and more preferably at least 24 months. In one embodiment, the liquid formulation disclosed herein remains stable at room temperature or, e.g., about 25° C., for at least 2 months, preferably at least 3 months, and more preferably at least 6 months.

In one embodiment, the stability of the formulation can be indicated by detecting changes in the appearance, visible particles, protein content, turbidity, purity and/or charge variants of the formulation. In one embodiment, the stability of the liquid formulation disclosed herein can be determined in a high temperature stress test, e.g., after storage at 40±2° C. for at least 1 week, 2 weeks or preferably 1 month, or in an accelerated test, e.g., after storage at 25±2° C. for at least 1 month or 2 months, or in a long-term test, e.g., after storage at 5±3° C. for at least 2 months or 3 months. In one embodiment, the stability of the liquid formulation disclosed herein is determined relative to an initial value, for example, an initial value on day 0 of storage.

In one embodiment, the liquid formulation disclosed herein remains a clear to slightly opalescent, colorless to pale yellow liquid free of particles in appearance after storage. In one embodiment, no visible particles exist in the formulation upon visual inspection under a clarity detector. In one embodiment, the liquid formulation disclosed herein is examined for stability after storage by determining the change in protein content, wherein the rate of change in protein content is no more than 20%, preferably no more than 10%, e.g., 7-8%, and more preferably no more than 5%, 2% or 1%, relative to an initial value, as measured, for example, by the ultraviolet spectrophotometry (UV) method. In one embodiment, the liquid formulation disclosed herein is examined for stability after storage by determining the change in purity of the liquid formulation disclosed herein, wherein the change in monomer purity (or change in main peak) is no more than 10%, e.g., no more than 5%, 4% or 3%, e.g., no more than 2%, preferably no more than 1%, relative to an initial value, as measured by size exclusion chromatography-high performance liquid chromatography (SEC-HPLC). In one embodiment, the liquid formulation disclosed herein is examined for stability after storage by determining the change in purity of the liquid formulation disclosed herein, wherein the change in monomer purity (or change in main peak) is reduced by no more than 10%, e.g., no more than 5%, 4%, 3%, 2% or 1%, relative to an initial value, as measured by non-reduced sodium dodecyl sulphate capillary electrophoresis (CE-SDS). In one embodiment, the liquid formulation disclosed herein is examined for stability after storage by cation exchange high performance liquid chromatography (CEX-HPLC), wherein the percent change in a charge variant (e.g., principal component, acidic component or basic component) in the formulation is no more than 40%, e.g., no more than 30% or no more than 20%; or the sum of percent changes in charge variants (principal component, acidic component and basic component) is no more than 60%, e.g., no more than 50% or no more than 40%, relative to an initial value.

In one embodiment, the quality criteria for the actual production process is that the liquid formulation disclosed herein is stable after storage, e.g., at 5±3° C. for at least 12 months, and preferably, has one or more of the following characteristics relative to an initial value on day 0 of storage:

(i) a purity of greater than 95%, preferably greater than 96%, 97%, 98% or 99%, as measured by SEC-HPLC;

(ii) a purity of greater than 90%, preferably greater than 95%, 96%, 97% or 98%, as measured by non-reduced CE-SDS;

(iii) a principal component content in the formulation of greater than 50%, preferably greater than 60% or 70%, as measured by CEX-HPLC; and (iv) a rate of change in protein content of less than 10%, preferably less than 5%, 4%, 3% or 2%, as measured by using the UV method.

In one aspect, the liquid formulation disclosed herein is a pharmaceutical formulation, preferably an injection, and more preferably a subcutaneous injection or an intravenous injection.

In another aspect, the present invention provides a solid antibody formulation obtained by solidifying the liquid antibody formulation disclosed herein. The solidification treatment is implemented by, e.g., crystallization, spray drying, or lyophilization. In one preferred embodiment, the solid antibody formulation is, e.g., in the form of a lyophilized powder for injection. The solid antibody formulation can be reconstituted in a suitable vehicle prior to use to give a reconstituted formulation of the present invention. The reconstituted formulation is also a liquid antibody formulation disclosed herein. In one embodiment, the suitable vehicle is selected from water for injection, organic solvents for injection (including but not limited to, oil for injection, ethanol, propylene glycol, and the like), and combinations thereof.

In one aspect, the present invention provides a delivery device comprising the liquid antibody formulation or the solid antibody formulation disclosed herein. In one embodiment, the delivery device disclosed herein is provided in the form of a pre-filled syringe comprising the liquid antibody formulation or the solid antibody formulation disclosed herein, e.g., for use in intravenous, subcutaneous, intradermal or intramuscular injection, or intravenous infusion.

In another aspect, the present invention provides a method for delivering the IL-23p19 antibody protein to a subject, e.g., a mammal, comprising administering the liquid antibody formulation or the solid antibody formulation disclosed herein to the subject, the delivery being implemented, e.g., using a delivery device in the form of a pre-filled syringe.

In yet another aspect, the present invention provides use of the liquid antibody formulation or the solid antibody formulation disclosed herein in preparing a delivery device, a pre-filled syringe or a medicament for treating immune system diseases, for example for treating autoimmune diseases or inflammation, wherein the diseases include (but are not limited to) psoriasis, Crohn's disease, rheumatoid arthritis, ankylosing spondylitis, psoriatic arthritis and the like.

Other embodiments of the present invention will become apparent by reference to the detailed description hereinafter.

BRIEF DESCRIPTION OF THE DRAWINGS

The preferred embodiments of the present invention described in detail below will be better understood when read in conjunction with the following drawings. For the purpose of illustrating the present invention, currently preferred embodiments are shown in the drawings. However, it should be understood that the present invention is not limited to accurate arrangement and means of the embodiments shown in the drawings.

DETAILED DESCRIPTION

Figure 1:
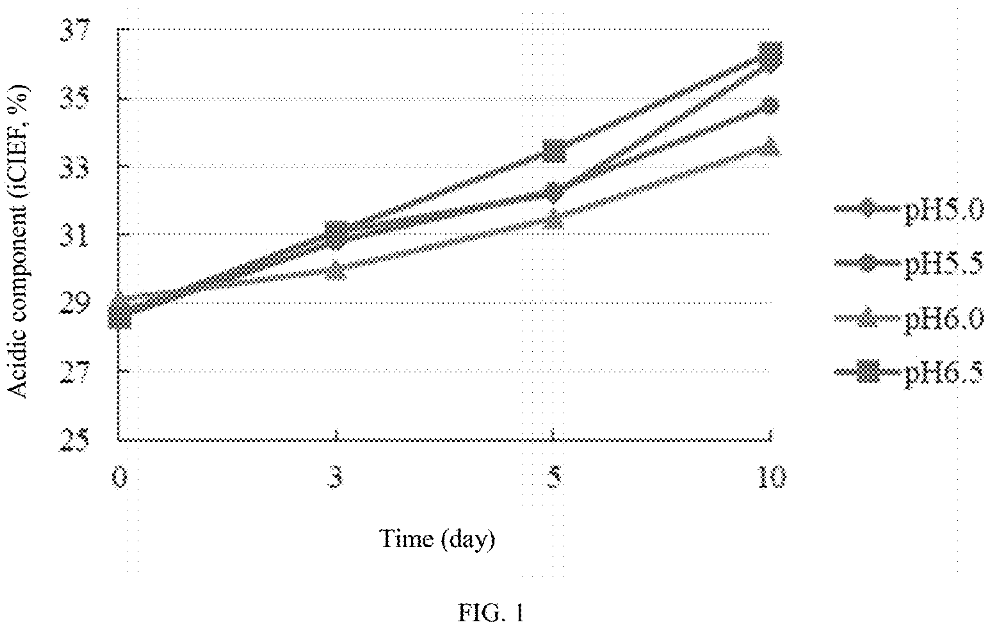
FIG. 1 a graph showing the change in charge variant-acidic component in a pH screening test (iCIEF, 40±2° C.).

Before the present invention is described in detail, it should be understood that the present invention is not limited to the particular methods or experimental conditions described herein since the methods and conditions may vary. Further, the terms used herein are for the purpose of describing particular embodiments only and are not intended to be limiting.

Definitions

Unless defined otherwise, all technical and scientific terms used herein have the same meaning as commonly understood by those of ordinary skill in the art. For the purposes of the present invention, the following terms are defined below.

The term "about" used in combination with a numerical value is intended to encompass the numerical values in a range from a lower limit less than the specified numerical value by 5% to an upper limit greater than the specified numerical value by 5%.

The term "and/or", when used to connect two or more options, should be understood to refer to any one of the options or any two or more of the options.

As used herein, the term "comprise" or "include" is intended to include the described elements, integers or steps, but not to exclude any other elements, integers or steps. As used herein, the term "comprise" or "include", unless indicated otherwise, also encompasses the situation where the entirety consists of the described elements, integers or steps. For example, when referring to an antibody variable region "comprising" a particular sequence, it is also intended to encompass an antibody variable region consisting of the particular sequence.

The p19 subunit of IL-23 (also referred to herein as "IL-23p19" or "p19 subunit") is a polypeptide having 189 amino acids, comprising a leader sequence of 21 amino acids (Oppmann et al., Immunity 13:715 (2000); SEQ ID NO: 181), and 4 packed alpha helices of A, B, C, and D, with an up-up-down-down topology. The 4 helices are linked by 3 polypeptide loops. A-B and C-D loops are relatively long as they link parallel helices. The short B-C loop links the B and C helices in reverse parallel. The p19 subunit of IL-23 is a member of the IL-6 family of helical cytokines. The cytokine family members bind to cognate receptors through three conserved epitopes (sites I, II, and III; Bravo and Heath (2000) EMBO J., 19:2399-2411). The p19 subunit interacts with 3 cytokine receptor subunits to form a competent signaling complex. When expressed in cells, the p19 subunit first forms a complex with the p40 subunit, and the p19 subunit shares the p40 subunit with IL-12. The pl9p40 complex is secreted from cells as a heterodimeric protein and is referred to as IL-23. In one embodiment, the IL-23p19 disclosed herein is derived from humans (NCBI: AAG37232) or cynomolgus monkeys (NCBI: AEY84629).

The term "anti-IL-23p19 antibody", "anti-IL-23p19", "IL-23p19 antibody" or "antibody binding to IL-23p19" as used herein refers to an antibody which can bind to human or cynomolgus monkey IL-23p19 subunit or fragment thereof with sufficient affinity so as to serve as a diagnostic agent and/or a therapeutic agent targeting human or cynomolgus monkey IL-23p19.

As used herein, the term "antibody" is used in the broadest sense, and refers to a protein comprising an antigen-binding site and encompasses natural and artificial antibodies with various structures, including but not limited to intact antibodies and antigen-binding fragments of antibodies.

The terms "whole antibody", "full-length antibody", "complete antibody" and "intact antibody" are used interchangeably herein to refer to a glycoprotein comprising at least two heavy chains (H) and two light chains (L) interconnected by disulfide bonds. Each heavy chain consists of a heavy chain variable region (abbreviated herein as VH) and a heavy chain constant region. Each heavy chain constant region consists of 3 domains CH1, CH2 and CH3. Each light chain consists of a light chain variable region (abbreviated herein as VL) and a light chain constant region. Each light chain constant region consists of one domain CL. The VH region and the VL region can be further divided into hypervariable regions (complementarity determining regions, or CDRs), with relatively conservative regions (framework regions, or FRs) inserted therebetween. Each VH or VL consists of three CDRs and four FRs, arranged from amino-terminus to carboxyl-terminus in the following order: FR1, CDR1, FR2, CDR2, FR3, CDR3 and FR4. The constant regions are not directly involved in binding of antibodies to antigens, but exhibit a variety of effector functions.

"Complementarity determining region" or "CDR region" or "CDR" is a region in an antibody variable domain that is highly variable in sequence and forms a structurally defined loop ("hypervariable loop") and/or comprises antigen-contacting residues ("antigen contact site"). CDRs are primarily responsible for binding to antigen epitopes. The CDRs of the heavy and light chains are generally referred to as CDR1, CDR2, and CDR3, and are numbered sequentially from the N-terminus. The CDRs located in the heavy chain variable domain of the antibody are referred to as HCDR1, HCDR2 and HCDR3, whereas the CDRs located in the light chain variable domain of the antibody are referred to as LCDR1, LCDR2 and LCDR3.

In a given amino acid sequence of a light chain variable region or a heavy chain variable region, the exact amino acid sequence boundary of each CDR can be determined using any one or a combination of many well-known antibody CDR assignment systems including, e.g., Chothia based on the three-dimensional structure of antibodies and the topology of the CDR loops (Chothia et al. (1989) *Nature* 342: 877-883; Al-Lazikani et al., Standard conformations for the canonical structures of immunoglobulins, *Journal of Molecular Biology,* 273: 927-948 (1997)), Kabat based on antibody sequence variability (Kabat et al., Sequences of Proteins of Immunological Interest, $4^{th}$ Ed., U.S. Department of Health and Human Services, National Institutes of Health (1987)), AbM (University of Bath), Contact (University College London), International ImMunoGeneTics database (IMGT) (imgt.cines.fr/ on the World Wide Web), and North CDR definition based on the affinity propagation clustering using a large number of crystal structures.

Unless otherwise stated, residue positions of an antibody variable region (including heavy chain variable region residues and light chain variable region residues) are numbered according to the Kabat numbering system (Kabat et al., Sequences of Proteins of Immunological Interest, 5th Ed. Public Health Service, National Institutes of Health, Bethesda, Md. (1991)).

In one embodiment, the boundaries of the CDRs of the antibody of the present invention are determined as per the AbM scheme.

"Antibody fragment" refers to a molecule different from an intact antibody, which comprises a portion of the intact antibody and binds to an antigen to which the intact antibody binds. Examples of the antibody fragment include, but are not limited to, Fv, Fab, Fab', Fab'-SH, F(ab')2; a diabody; a linear antibody; a single-chain antibody (e.g., scFv); a single-domain antibody; a bivalent or bispecific antibody or a fragment thereof; a Camelidae antibody; and a bispecific antibody or multispecific antibody formed from antibody fragments.

The term "antibody formulation" refers to a preparation in a form that allows the biological activity of an antibody as an active ingredient to be exerted effectively, and does not contain other components having unacceptable toxicity to a subject to which the formulation is to be administered. Such antibody formulations are generally sterile. Generally, the antibody formulation comprises a pharmaceutically acceptable excipient. A "pharmaceutically acceptable" excipient is an agent that can be reasonably administered to a mammal subject so that an effective dose of the active ingredient used in the formulation can be delivered to the subject. The concentration of the excipient is adapted to the mode of administration and may, for example, be acceptable for injection.

The term "anti-IL-23p19 antibody formulation", herein also referred to as the "antibody formulation disclosed herein", refers to a preparation comprising an anti-IL-23p19 antibody protein as an active ingredient and a pharmaceutically acceptable excipient. The anti-IL-23p19 antibody protein, as the active ingredient, is suitable for therapeutic or prophylactic administration to a human or non-human animal after the anti-IL-23p19 antibody protein is combined with the pharmaceutically acceptable excipient. The antibody formulation disclosed herein can be prepared, for example, as an aqueous liquid formulation, e.g., in a ready-to-use pre-filled syringe, or as a lyophilized formulation to be reconstituted (i.e., redissolved) by dissolution and/or suspension in a physiologically acceptable solution immediately prior to use. In some embodiments, the anti-IL-23p19 antibody protein formulation is in the form of a liquid formulation.

A "stable" antibody formulation refers to a formulation where the antibody retains an acceptable degree of physical and/or chemical stability after storage in specific conditions, after shaking and/or after repeated freezing-thawing. Although the antibody in the antibody formulation may not maintain 100% of its chemical structure after storage for a specific period of time, shaking or repeated freezing-thawing, the antibody formulation is considered "stable" when about 90%, about 95%, about 96%, about 97%, about 98%, or about 99% of the antibody structure or function is generally maintained after storage for a specific period of time. In some specific embodiments, the anti-IL-23p19 antibody protein formulation disclosed herein shows undetectable antibody aggregation or degradation or chemical modification during manufacture, preparation, transportation and long-term storage, and therefore there is little or even no loss of biological activity in the anti-IL-23p19 antibody protein; the anti-IL-23p19 antibody protein shows high stability.

A variety of analytical techniques are known in the art for determining the stability of proteins, see, e.g., *Peptide and Protein Drug Delivery,* 247-301, Vincent Lee Ed., Marcel Dekker, Inc., New York, N.Y., Pubs (1991) and Jones, *A. Adv. Drug Delivery Rev.* 10: 29-90 (1993). Stability can be determined at a selected temperature and for a selected storage time. For example, the storage time can be selected based on the expected shelf life of the formulation. Alternatively, an accelerated stability test can be adopted. In some embodiments, the stability test is performed by conducting various stress tests on the antibody formulation. These tests can represent extreme conditions that a formulated antibody formulation may encounter during manufacture, storage or transportation, and can also represent conditions that may accelerate the instability of the antibody in the antibody formulation during a non-manufacture, -storage or -transportation process. For example, a glass vial can be filled with the formulated anti-IL-23p19 antibody protein formulation so as to examine the antibody for stability under high temperature stress. The antibody can be considered to "maintain its physical stability" in the formulation if the formulation does not exhibit aggregation, precipitation, turbidity and/or denaturation, or exhibits very little aggregation, precipitation, turbidity, and/or denaturation after storage for a period of time. Safety issues arise as the aggregation of antibodies in the formulation can potentially lead to an increased immune response in a patient. Accordingly, there is a need to minimize or prevent the aggregation of antibodies in the formulation. SEC-HPLC can be used to determine soluble aggregates in the formulation. In addition, the stability of the formulation can be indicated by visually inspecting the appearance, color and/or clarity of the formulation, or by detecting the turbidity of the formulation by the $OD_{350\ nm}$ method, or by determining the purity of the formulation by the non-reduced CE-SDS method. In one embodiment, the stability of the formulation is measured by determining the percentage of antibody monomer after storage at a particular temperature for a particular period of time, wherein a higher percentage of antibody monomer in the formulation indicates higher stability of the formulation.

An "acceptable degree" of physical stability can represent that at least about 90% of anti-IL-23p19 antibody protein monomer is detected in the formulation after storage at a particular temperature for a particular period of time. In some embodiments, an acceptable degree of physical stability represents at least about 90%, 91%, 92%, 93%, 94%, 95%, 96%, 97%, 98% or 99% of anti-IL-23p19 antibody protein monomer after storage at a particular temperature for at least 2 weeks, at least 28 days, at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, at least 24 months, or longer. When the physical stability is assessed, the particular temperature at which the pharmaceutical formulation is stored can be any temperature from about −80° C. to about 45° C., e.g., about −80° C., about −30° C., about −20° C., about 0° C., about 4-8° C., about 5° C., about 25° C., about 35° C., about 37° C., about 40° C., about 42° C., or about 45° C.

The antibody can be considered to "maintain its chemical stability" in the formulation if the antibody in the formulation does not exhibit significant chemical changes after storage for a period of time. Most of the chemical instability results from the formation of covalently modified forms of the antibody (e.g., charge variants of the antibody). Basic variants can be formed, for example, by aspartic acid isomerization, and N- and C-terminal modifications; acidic variants can be produced by deamidation, sialylation and saccharification. Chemical stability can be assessed by detecting and/or quantifying chemically altered forms of the antibody. For example, charge variants of the antibody in the formulation can be detected by cation exchange chromatography (CEX) or imaged capillary isoelectric focusing (iCIEF). In one embodiment, the stability of the formulation is measured by determining the percent change in charge variants of the antibody in the formulation after storage at a specific temperature for a specific period of time, wherein the smaller the change, the higher the stability of the formulation. An "acceptable degree" of chemical stability can represent that the percent change in a charge variant (e.g., principal component, acidic component or basic component) in the formulation is no more than 40%, e.g., no more than 30% or no more than 20%, or the sum of percent changes in charge variants (principal component, acidic component and basic component) is no more than 60%, e.g., no more than 50% or no more than 30%, after storage at a particular temperature for a particular period of time. In some embodiments, an acceptable degree of chemical stability can represent a percent change in charge variant-principal component not more than about 50%, 40%, 30%, 20% or 15% or a sum of percent change in charge variants not more than about 60%, 50% or 30%, after storage at a specific temperature for at least 2 weeks, at least 28 days, at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, at least 24 months, or longer. When the chemical stability is assessed, the temperature at which the pharmaceutical formulation is stored can be any temperature from about −80° C. to about 45° C., e.g., about −80° C., about −30° C., about −20° C., about 0° C., about 4-8° C., about 5° C., about 25° C., or about 45° C.

The term "lyophilized formulation" refers to a composition obtained or obtainable by a lyophilization process of a liquid formulation. Preferably, it is a solid composition having a water content of less than 5%, preferably less than 3%.

The term "reconstituted formulation" refers to a liquid formulation obtained by dissolving and/or suspending a solid formulation (e.g., a lyophilized formulation) in a physiologically acceptable solution.

As used herein, the term "room temperature" refers to a temperature from 15° C. to 30° C., preferably from 20° C. to 27° C., and more preferably 25° C.

"Stress conditions" refer to environments that are chemically and/or physically unfavorable to antibody proteins and may result in unacceptable destabilization of the antibody proteins, e.g., high temperature, shaking and freezing-thawing. "High temperature stress" refers to storing the antibody formulation at room temperature or higher (e.g., 40±2° C.)

for a period of time. The stability of the antibody formulation can be determined through a high temperature stress accelerated test.

As used herein, the term "parenteral administration" refers to administrations other than intraintestinal and topical administrations, typically by injection or infusion, including but not limited to, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. In some embodiments, the stable anti-IL-23p19 antibody formulation disclosed herein is administered parenterally to a subject. In one embodiment, the anti-IL-23p19 antibody formulation disclosed herein is administered by subcutaneous, intradermal, intramuscular or intravenous injection to a subject.

I. Antibody Formulation

The present invention provides a stable liquid antibody formulation comprising (i) an anti-IL-23p19 antibody, (ii) a buffer, (iii) a stabilizer, and (iv) a surfactant, wherein the antibody formulation has a pH of about 5.2-6.3. In one preferred embodiment, the liquid antibody formulation disclosed herein is in the form of an injection.

(i) Anti-IL-23p19 Antibody

In some embodiments, the anti-IL-23p19 antibody in the antibody formulation disclosed herein comprises: a heavy chain variable region (VH) of SEQ ID NO: 7 or a VH having at least 90% identity thereto; and a light chain variable region (VL) of SEQ ID NO: 8 or a VL having at least 90% identity thereto.

In some embodiments, the anti-IL-23p19 antibody in the antibody formulation disclosed herein comprises the VH CDR1, VH CDR2 and VH CDR3 sequences of the heavy chain variable region set forth in SEQ ID NO: 7, and the VL CDR1, VL CDR2 and VL CDR3 sequences of the light chain variable region set forth in SEQ ID NO: 8. In one embodiment, the anti-IL-23p19 antibody disclosed herein comprises a VH CDR1 of SEQ ID NO: 1, a VH CDR2 of SEQ ID NO: 2 and a VH CDR3 of SEQ ID NO: 3; and a VL CDR1 of SEQ ID NO: 4, a VL CDR2 of SEQ ID NO: 5 and a VL CDR3 of SEQ ID NO: 6.

In some embodiments, the anti-IL-23p19 antibody in the antibody formulation disclosed herein can comprise a heavy chain variable region (VH) having at least 90%, 95%, 98%, or 99% or higher identity to SEQ ID NO: 7; and/or a light chain variable region (VL) having at least 90%, 95%, 98%, or 99% or higher identity to SEQ ID NO: 8. As used herein, the term "sequence identity" refers to the degree to which sequences are identical on a nucleotide-by-nucleotide or amino acid-by-amino acid basis in a comparison window. The "percent sequence identity" can be calculated by the following steps: comparing two optimally aligned sequences in a comparison window; determining a number of positions in which nucleic acid bases (e.g., A, T, C, G and I) or amino acid residues (e.g., Ala, Pro, Ser, Thr, Gly, Val, Leu, Ile, Phe, Tyr, Trp, Lys, Arg, His, Asp, Glu, Asn, Gln, Cys, and Met) are the same in the two sequences to give the number of matched positions; dividing the number of matched positions by the total number of positions in the comparison window (i.e., the window size); and multiplying the result by 100 to give a percent sequence identity. Optimal alignment for determining the percent sequence identity can be achieved in a variety of ways known in the art, for example, using publicly available computer software such as BLAST, BLAST-2, ALIGN, or Megalign (DNASTAR) software. Those skilled in the art can determine suitable parameters for alignment of the sequences, including any algorithms necessary to achieve optimal alignment in a full-length sequence range or target sequence region being compared.

In some embodiments, the VH sequence of the antibody disclosed herein has no more than 10, preferably no more than 5, 4 or 3 different residues as compared to SEQ ID NO: 7, wherein preferably, the different residues are conservative amino acid substitutions. In some embodiments, the VL sequence of the antibody disclosed herein has no more than 10, preferably no more than 5, 4 or 3 different residues as compared to SEQ ID NO: 8, wherein preferably, the different residues are conservative amino acid substitutions. The "conservative substitution" refers to an amino acid alteration that results in the replacement of an amino acid with a chemically similar amino acid. Conservative substitution tables providing functionally similar amino acids are well known in the art.

In some embodiments, the anti-IL-23p19 antibody in the antibody formulation disclosed herein is an antibody in IgG form. "Antibody in the IgG form of IgG" refers to the heavy chain constant region of the antibody belonging to the IgG form. Heavy chain constant regions of all antibodies of the same IgG subtype are identical, and heavy chain constant regions of antibodies of different IgG subtypes are different. For example, an antibody in the form of IgG1 refers to the Ig domain of its heavy chain constant region being an Ig domain of IgG1.

In one embodiment of the present invention, substitution mutations (M252Y/S254T/T256E) are introduced in the Fc region of the antibody disclosed herein to enhance the ability of binding to human FcRn, in order to extend the half-life in vivo.

In one preferred embodiment, the anti-IL-23p19 antibody in the antibody formulation disclosed herein is the anti-IL-23p19 antibody 17D1-YTE disclosed in PCT/CN2019/121261 (International Application Date: Nov. 27, 2019), having a heavy chain of SEQ ID NO: 9 and a light chain of SEQ ID NO: 10. In one embodiment, the anti-IL-23p19 antibody is a purified IgG1 antibody produced by recombinant expression in CHO cells.

The amount of antibody or antigen-binding fragment thereof in the antibody formulation disclosed herein can vary with the specific desired characteristics of the formulation, the specific environment, and the specific purpose for which the formulation is used. In some embodiments, the antibody formulation is a liquid formulation, wherein the IL-23p19 antibody is at a concentration of about 1-300 mg/mL. In another embodiment, the IL-23p19 antibody in the liquid antibody formulation disclosed herein is at a concentration of about 25-250 mg/mL, preferably 50-200 mg/mL, e.g., about 50, 60, 70, 80, 90, 100, 110, 120, 130, 140, 150, 160, 170, 180, 190 or 200 mg/mL.

(ii) Buffer

Buffers are reagents that can control the pH of a solution within an acceptable range. In some embodiments, the buffer for use in the formulation disclosed herein can control the pH of the formulation disclosed herein at about 5.0-6.0, e.g., about 5.5-6.0. In some specific embodiments, the antibody formulation disclosed herein has a pH of about 5.2, 5.3, 5.4, 5.5, 5.6, 5.7, 5.8, 5.9, 6.0, 6.1, 6.2 or 6.3. For example, the antibody formulation disclosed herein has a pH of 5.5±0.3 or 6.0±0.3, preferably a pH of 6.0.

In some embodiments, the formulation disclosed herein comprise a buffer system selected from: a histidine-histidine hydrochloride buffer system, a citric acid-sodium citrate buffer system, an acetic acid-sodium acetate buffer system and a phosphate buffer system, preferably, a histidine-histidine hydrochloride buffer system.

In some embodiments, the buffer in the formulation disclosed herein is selected from histidine, histidine hydrochloride and a combination thereof. In some embodiments, the histidine in the buffer disclosed herein is at a concentration of about 0.775-3.1 mg/mL; preferably, the histidine is at a concentration of about 1.55 mg/mL. In another embodiment, the buffer used in the formulation disclosed herein consists of histidine and histidine hydrochloride, having a histidine content of about 0.38-1.52 mg/mL and a histidine hydrochloride content of about 0.54-2.16 mg/mL; preferably, the histidine and the histidine hydrochloride are at concentrations of about 0.76 mg/mL and about 1.08 mg/mL, respectively.

(iii) Stabilizer

Suitable stabilizers for use in the present invention can be selected from saccharides, polyols and amino acids and a combination thereof. Saccharides that may be used as a stabilizer include, but are not limited to, sucrose, trehalose, maltose, and a combination thereof. Polyols that may be used as a stabilizer include, but are not limited to, sorbitol, mannitol, and a combination thereof. Amino acids that may be used as a stabilizer include, but are not limited to, arginine, arginine hydrochloride, methionine, glycine, proline, and a combination thereof.

For example, in some embodiments, the stabilizer comprises one or more selected from: In one embodiment, the liquid formulation disclosed herein comprises sorbitol as the sole stabilizer. In this embodiment, the amount of sorbitol in the liquid formulation disclosed herein may be about 25-100 mg/mL, e.g., 40-60 mg/mL. For example, sorbitol may be present in an amount of about 40, 42, 44, 46, 48, 50, 52, 54, 56, 58 or 60 mg/mL, preferably about 50 mg/mL.

In one embodiment, the liquid formulation disclosed herein comprises a combination of sorbitol and arginine as the stabilizer. In the combination, sorbitol may be present in an amount of about 15-60 mg/mL, preferably 20-40 mg/mL, e.g., about 20, 25, 30, 35 or 40 mg/mL. In the combination, arginine may be present in an amount of about 6.97-27.88 mg/mL, preferably 10.45-17.42 mg/mL, particularly about 13.94 mg/mL. Preferably, the liquid formulation disclosed herein comprises sorbitol at about 20-40 mg/mL and arginine at about 10.45-17.42 mg/mL. More preferably, the liquid formulation disclosed herein comprises sorbitol at about 30 mg/mL and arginine at about 13.94 mg/mL.

In one embodiment, the liquid formulation disclosed herein comprises sucrose as the sole stabilizer. In this embodiment, the amount of sucrose in the liquid formulation disclosed herein may be about 40-160 mg/mL, preferably 70-90 mg/mL; for example, sucrose may be present in an amount of about 70, 75, 80, 85 or 90 mg/mL, preferably about 80 mg/mL.

In one embodiment, the liquid formulation disclosed herein comprises a combination of sucrose and arginine as the stabilizer. In the combination, sucrose may be present in an amount of about 25-100 mg/mL, preferably 40-60 mg/mL, e.g., 40, 42, 44, 46, 48, 50, 52, 54, 56, 58 or 60 mg/mL. In the combination, arginine may be present in an amount of about 6.97-27.88 mg/mL, preferably 10.45-17.42 mg/mL, particularly about 13.94 mg/mL. Preferably, the liquid formulation disclosed herein comprises sucrose at about 40-60 mg/mL and arginine at about 10.45-17.42 mg/mL. More preferably, the liquid formulation disclosed herein comprises sucrose at about 50 mg/mL and arginine at about 13.94 mg/mL.

(iv) Surfactant

As used herein, the term "surfactant" refers to an organic substance with an amphiphilic structure; that is, the structure is composed of groups with opposite solubility tendencies, typically an oil-soluble hydrocarbon chain and a water-soluble ionic group.

In one embodiment, the surfactant in the liquid formulation disclosed herein is a non-ionic surfactant, e.g., alkyl poly(ethylene oxide). Specific non-ionic surfactants that can be contained in the formulation disclosed herein include, for example, polysorbates such as polysorbate 20, polysorbate 80, polysorbate 60 or polysorbate 40, poloxamer, and the like. In one preferred embodiment, the liquid formulation disclosed herein comprises polysorbate 80 or polysorbate 20 as the surfactant.

The amount of the surfactant in the antibody formulation disclosed herein can vary with the specific desired characteristics of the formulation, the specific environment, and the specific purpose for which the formulation is used. In some preferred embodiments, the formulation may comprise a surfactant, particularly polysorbate 80, at about 0.1-1 mg/mL, preferably about 0.2-0.8 mg/mL, e.g., about 0.2, 0.3, 0.4, 0.5, 0.6, 0.7 or 0.8 mg/mL, and preferably comprise polysorbate 80 at about 0.5 mg/mL.

(v) Other Excipients

The liquid antibody formulation disclosed herein may or may not comprise other excipients. Such other excipients include, for example, antimicrobials, antistatic agents, antioxidants, chelating agents, gelatin, and the like. These and other known pharmaceutical excipients and/or additives suitable for use in the formulation disclosed herein are well known in the art, for example, as listed in "*The Handbook of Pharmaceutical Excipients,* 4th edition, edited by Rowe et al., American Pharmaceuticals Association (2003); and *Remington: the Science and Practice of Pharmacy,* 21st edition, edited by Gennaro, Lippincott Williams & Wilkins (2005)".

II. Preparation of Formulation

The present invention provides a stable formulation comprising an anti-IL-23p19 antibody protein. The anti-IL-23p19 antibody protein used in the formulation disclosed herein can be prepared using techniques known in the art for the production of antibodies. For example, the antibody can be recombinantly prepared. In one preferred embodiment, the antibody disclosed herein is recombinantly prepared in 293 cells or CHO cells.

The use of antibodies as active ingredients in drugs is now very common. Techniques for purifying therapeutic antibodies to pharmaceutical grade are well known in the art. For example, Tugcu et al. (Maximizing productivity of chromatography steps for purification of monoclonal antibodies, *Biotechnology and Bioengineering* 99 (2008) 599-613) described a monoclonal antibody three-column purification method in which ion exchange chromatography (anionic IEX and/or cationic CEX chromatography) is used after a protein A capture step. Kelley et al. (Weak partitioning chromatography for anion exchange purification of monoclonal antibodies, *Biotechnology and Bioengineering* 101 (2008) 553-566) described a two-column purification method in which a weak partitioning anion exchange resin is used after protein A affinity chromatography.

Generally, monoclonal antibodies recombinantly produced can be purified using conventional purification methods to provide a drug substance with sufficient reproducibility and proper purity for the formulation of antibody formulations. For example, after the antibody is secreted from the recombinant expression cells into the culture medium, the supernatant of the expression system can be concentrated using a commercially available protein concentration filter, e.g., Amicon ultrafiltration device. Then the antibody can be purified by methods such as chromatography, dialysis and affinity purification. Protein A is suitable as an affinity ligand for the purification of IgG1, IgG2 and IgG4 antibodies. Other antibody purification methods, such as ion exchange chromatography, can also be used. After the antibody with sufficient purity is obtained, a formulation comprising the antibody can be prepared according to methods known in the art.

For example, the preparation can be performed by the following steps: (1) removing impurities such as cells from fermentation broth by centrifuging and clarifying after the fermentation to give a supernatant; (2) capturing an antibody using affinity chromatography (e.g., a protein A column with specific affinity for IgG1, IgG2 and IgG4 antibodies); (3) inactivating viruses; (4) purifying (usually CEX cation exchange chromatography can be adopted) to remove impurities in a protein; (5) filtering the viruses (to reduce the virus titer by, e.g., more than 4 log 10); and (6) ultrafiltering/diafiltering (which can be used to allow the protein to be exchanged into a formulation buffer that is favorable for its stability and concentrated to a suitable concentration for injection). See, e.g., B. Minow, P. Rogge, K. Thompson, *BioProcess International*, Vol. 10, No. 6,2012, pp. 48-57.

III. Analytical Method of Formulation

Biologics stability studies typically include real-time stability studies in actual storage conditions (long-term stability studies), accelerated stability studies and forced condition studies. For the stability studies, the study conditions are explored and optimized according to the purpose and the characteristics of the product; stability study schemes, such as long-term, accelerated and/or forced condition tests and the like, should be established according to various influencing factors. Accelerated and forced condition studies are beneficial to understanding the stability of the product in short-term deviations from storage conditions and in extreme conditions, and provide supporting data for the determination of the shelf life and storage conditions.

During the storage of antibody formulations, antibodies may undergo aggregation, degradation or chemical modification, resulting in antibody heterogeneity (including size heterogeneity and charge heterogeneity), aggregates and fragments, etc., which may affect the quality of the antibody formulations. Accordingly, it is necessary to monitor the stability of antibody formulations.

Various methods are known in the art for testing the stability of antibody formulations. For example, the purity of the antibody formulation can be analyzed and the aggregation level of the antibody can be evaluated by methods such as reduced CE-SDS, non-reduced CE-SDS and SEC-HPLC; charge variants in the antibody formulation can be analyzed by capillary isoelectric focusing electrophoresis (cIEF), imaged capillary isoelectric focusing (iCIEF), ion exchange chromatography (IEX), and the like. In addition, the stability of the formulation can be determined quickly by visually inspecting the appearance of the formulation. In addition, the change in protein content in the formulation can be detected by ultraviolet spectrophotometry (UV method).

Non-reduced CE-SDS is a method for determining the purity of antibodies using a capillary as a separation channel. In CE-SDS, protein migration is driven by the surface charge caused by SDS binding, which is proportional to the molecular weight of the protein. Since all SDS-protein complexes have similar mass-to-charge ratios, electrophoretic separation based on the size or hydrodynamic radius of the molecules can be achieved in the molecular sieve gel matrix of the capillary. This method has been widely used to monitor the purity of denatured intact antibodies. Generally, in non-reduced CE-SDS, the test sample is mixed with an SDS sample buffer and iodoacetamide. Then, the mixture can be incubated at 68-72° C. for about 10-15 min, cooled to room temperature, and centrifuged, and then the supernatant is analyzed. The protein migration is detected using an ultraviolet detector to give an electropherogram. The purity of the antibody formulation can be calculated as the percentage of the IgG main peak area to the sum of all peak areas. For further description of CE-SDS, see, e.g., Richard R. et al., Application of CE SDS gel in development of biopharmaceutical antibody-based products, *Electrophoresis,* 2008, 29,3612-3620.

Size exclusion chromatography-high performance liquid chromatography (SEC-HPLC) is another important method for the standardization and quality control of antibodies. In this method, molecules are separated mainly based on the differences in their size or hydrodynamic radius. Antibodies can be separated in three main forms by SEC-HPLC: high-molecular-weight species (HMMS), main peak (mainly antibody monomer), and low-molecular-weight species (LMMS). The purity of the antibody can be calculated as the percentage of the main peak area to the sum of all peak areas on the chromatogram. The percentage of antibody monomer in the formulation can be measured by SEC-HPLC, which gives information about the content of soluble aggregates and splices. For further description of SEC-HPLC, see, e.g., *J. Pharm. Scien.,* 83: 1645-1650, (1994); *Pharm. Res.,* 11: 485 (1994); *J. Pharm. Bio. Anal.,* 15: 1928 (1997); *J. Pharm. Bio. Anal.,* 14: 1133-1140 (1986). In addition, see also, e.g., R. Yang et al., High resolution separation of recombinant monoclonal antibodies by size exclusion ultra-high performance liquid chromatography (SE-UHPLC), *Journal of Pharmaceutical and Biomedical Analysis* (2015), http://dx.doi.org/10.1016/j.jpba.2015.02.032; and Alexandre Goyon et al., Protocols for the analytical characterization of therapeutic monoclonal antibodies, I-Non-denaturing chromatographic techniques, *Journal of Chromatography*, http://dx.doi.org/10.1016/j.jchromb.2017.05.010.

The charge variants of the antibody in the antibody formulation can be determined by cation exchange high performance liquid chromatography (CEX-HPLC). In this method, peaks eluted from the CEX-HPLC column earlier than the retention time of the main peak (or principal component) are labeled as "acidic peaks" (or acidic component), while those eluted from the CEX-HPLC column later than the retention time of the main peak are labeled as "basic peaks" (or basic component).

Accelerated stability studies can be used to check the stability of products, which facilitates the screening of stable pharmaceutical formulations. For example, formulation samples can be placed at an elevated temperature, e.g., about 40±2° C. or 25±2° C. for an accelerated stability study. The test indexes for product stability may include appearance, visible particles, protein content, turbidity, purity (SEC-HPLC and non-reduced CE-SDS) and charge variants (iCIEF and CEX-HPLC).

IV. Use of Formulation

The present invention provides a formulation for treating IL-23 associated diseases in a subject. The subject may be a mammal, e.g., a primate, preferably a higher primate, e.g., a human (e.g., a patient suffering from or at risk of suffering from the disease described herein). In one embodiment, the subject has or is at risk of having the disease described herein (e.g., IL-23 associated diseases described herein, e g., immune system diseases (such as autoimmune diseases or inflammation)). In certain embodiments, the subject is receiving or has received other therapies, e.g., anti-inflammatory drugs or immunosuppressive therapy and/or radiotherapy.

In some embodiments, the IL-23 associated diseases described herein include immune system diseases, e.g., autoimmune diseases and inflammation. The disease includes (but is not limited to) psoriasis, Crohn's disease, rheumatoid arthritis, ankylosing spondylitis, psoriatic arthritis and the like.

In one embodiment, the immune system disease is a disease that expresses an elevated level of IL-23p19.

In some embodiments, the method for preventing or treating disclosed herein further comprises administering to the subject or individual the antibody molecule, the pharmaceutical composition or the immunoconjugate disclosed herein in combination with one or more additional therapies, e.g., therapeutic modalities and/or other therapeutic agents.

The present invention further provides use of the formulation disclosed herein in preparing a medicament for delivering an anti-IL-23p19 antibody protein to a mammal.

The antibody formulation disclosed herein can be administered to a subject or a patient in a variety of routes. For example, the administration can be performed by infusion or by using a syringe. Accordingly, in one aspect, the present invention provides a delivery device (e.g., a syringe) comprising the antibody formulation disclosed herein (e.g., a pre-filled syringe). The patient will receive an effective amount of the anti-IL-23p19 antibody protein as the primary active ingredient, i.e., an amount sufficient to treat, ameliorate or prevent the disease or disorder of interest. The therapeutic effect can include a reduction in physiological symptoms. The optimal effective amount and concentration of the antibody for any specific subject will depend on a variety of factors including the age, weight, health status and/or sex of the patient, the nature and extent of the disease, the activity of the specific antibody, its clearance in the body, as well as any other possible treatments administered in combination with the antibody formulation. For a specific case, the effective amount delivered can be determined based on the judgment of a clinician.

The following examples are described to assist in understanding the present invention. The examples are not intended to be and should not be interpreted in any way as limiting the protection scope of the present invention.

Abbreviations

| Abbreviation | Full name |
|---|---|
| CE-SDS | Sodium dodecyl sulphate capillary electrophoresis |
| CEX-HPLC | Cation exchange high performance liquid chromatography |
| ELISA | Enzyme-linked immunosorbent assay |
| SEC-HPLC | Size exclusion chromatography-high performance liquid chromatography |
| iCIEF | Imaged capillary isoelectric focusing |

DETAILED DESCRIPTION

The anti-IL-23p19 antibody 17D1-YTE disclosed herein, an antibody independently developed by the assignee Innovent Biologics (Suzhou) Co., Ltd., was disclosed in PCT Application No. PCT/CN2019/121261.

In order to develop a simple and easy-to-use injection formulation formula suitable for long-term stable storage of the antibody disclosed herein, the influence of different pH values and the content of different stabilizers on quality of the antibody protein was investigated through 40° C. forced and 25° C. accelerated stability tests, and finally, a formulation formula favorable for the stability of the antibody was selected. The materials and methods used throughout the study are as follows:

Materials and Methods 1.1. Materials

| Name | Grade | Manufacturer & brand | Catalog No. | Criteria |
|---|---|---|---|---|
| Citric acid (anhydrous) | Pharmaceutical grade | Merck, Germany | 1.00241.5000 | Ch. P, USP |
| Sodium citrate dihydrate | Pharmaceutical grade | Merck, Germany | 1.37042.5000 | Ch. P, USP |
| Histidine | Pharmaceutical grade | Ajinomoto, Shanghai | 1.04352.1000 | *Ch. P* (2015 Edition), *USP*, *JP* |
| Histidine hydrochloride | Pharmaceutical grade | Merck, Germany | 1.04354.0500 | *Ch. P* (2015 Edition) |
| Sorbitol | Pharmaceutical grade | Roquette, French | H20110265 | *EP, BP, NF, USP, Ch. P* (2015 edition) |
| Sucrose | Pharmaceutical grade | Merck, Germany | 1.00892.9050 | *Ch. P* (2015 Edition), *USP* |
| Arginine | Pharmaceutical grade | Merck, Germany | 1.01544.1000 | *Ph Eur, BP, JP, USP, Ch. P* (2015 Edition) |
| Polysorbate 80 | Pharmaceutical grade | Well, Nanjing | Jiangsu MPA Approval No. F15423203 | *Ch. P* (2015 Edition) |
| Hydrochloric acid | Pharmaceutical grade | Merck, Germany | 1.00314.2508 | *Ph Eur, BP, JP, NF, Ch. P* (2015 Edition) |

Note:
N/A denotes not applicable.

1.2. Instruments and Equipment

| Name | Manufacturer & brand | Model No. | No. |
|---|---|---|---|
| Electronic balance | Sartorius, Germany | BSA3202S | PD-A1-186 |
| Constant temperature and humidity chamber | BINDER, Germany | KBF P 720 | PD-A1-070 |
| Biochemical incubator | Jinghong, Shanghai | SHP-150 | PD-A1-200 |

-continued

| Name | Manufacturer & brand | Model No. | No. |
|---|---|---|---|
| Medical refrigerator | Haier, Qingdao | HYC-360 | PD-A1-165 |
| Ultra-low temperature freezer | Thermo, USA | 907 | PD-A1-175 |
| Clarity detector | Tianda Tianfa, Tianjin | YB-2 | PD-A1-033 |
| Ultraviolet-visible spectrophotometer | Shimadzu, Japan | UV-1800 | AS-A1-037 |
| pH meter | Mettler, Switzerland | FE20 | PD-A1-161 |
| Multi-channel microspectrophotometer | Thermo, USA | Nanodrop 8000 | PD-A1-052 |
| Benchtop refrigerated centrifuge | Thermo, USA | SL16R | PD-A1-082 |
| Clean bench | Airtech, Suzhou | SW-CJ-2FD | QC-A1-011 |
| Medium-flow manual peristaltic pump | Watson Marlow, UK | 520S/R2 | PD-A1-235 |
| Filling machine | Watson Marlow, Denmark | FP50 | PD-C14-115 |
| Insoluble particle detector | Tianda Tianfa, Tianjin | GWJ-8 | QC-A1-094 |

1.3. Items and Methodology for Formulation Stability Tests

The test items in the whole studies include: (1) the appearance and the presence of visible particles; (2) the protein content in the formulation determined by the ultraviolet method (UV method); (3) the purity of the antibody formulation determined by size exclusion chromatography-high performance liquid chromatography (SEC-HPLC) and expressed as the percentage of the main peak area to the sum of all peak areas; (4) the purity of the antibody formulation determined by non-reduced sodium dodecyl sulphate capillary electrophoresis (non-reduced CE-SDS) and expressed as the percentage of the main peak area to the sum of all peak areas; (5) charge variants in the antibody formulation determined by CEX-HPLC expressed as the percentages of the principal component, acidic component and basic component; and (6) charge variants in the antibody formulation determined by iCIEF expressed as the percentages of the principal component, acidic component and basic component.

Detection of Visible Particles and Insoluble Particles

According to the method described in *Pharmacopoeia of the People's Republic of China*, the visible particles in the sample are detected using a clarity detector (model No. YB-2, Tianda Tianfa, Tianjin), and the insoluble particles in the sample are detected using an insoluble particle detector (model No. GWJ-8, Tianda Tianfa, Tianjin).

Determination of Protein Content

The protein content in the sample is determined using an ultraviolet spectrophotometer (model No. UV-1800, Shimadzu, Japan) and a multi-channel microspectrophotometer (model No. Nanodrop 8000, Thermo, USA).

Purity (SEC-HPLC)

The separation is performed using a size exclusion chromatographic column. The mobile phase is a phosphate buffer (3.12 g of sodium dihydrogen phosphate dihydrate, 8.77 g of sodium chloride and 34.84 g of arginine are dissolved in ultra-pure water, the pH of the solution is adjusted to 6.8 by adding hydrochloric acid, and the volume is brought to 1000 mL). The chromatographic column protective solution is 0.05% (w/v) $NaN_3$, the sample injection volume is 50 μL, the flow rate is 0.5 mL/min, the collection time is 30 min, the column temperature is 25° C., and the detection wavelength is 280 nm. The sample is diluted to 2 mg/mL with ultra-pure water for use as a sample solution. The formulation buffer is diluted in the same manner as described above to prepare a blank solution. The blank solution and the sample solution are separately injected into a liquid chromatograph in an amount of 50 μL for determination.

Purity (Non-Reduced CE-SDS)

The determination is conducted by capillary gel electrophoresis. The capillary is an uncoated capillary having an inner diameter of 50 μm, a total length of 30.2 cm and an effective length of 20.2 cm. Before electrophoresis, the capillary column is washed with 0.1 mol/L sodium hydroxide, 0.1 mol/L hydrochloric acid, ultra-pure water, and electrophoresis gel at 70 psi. The test sample is diluted to 2.0 mg/mL with an appropriate amount of ultra-pure water. 50 μL of the diluted sample is transferred into a 1.5 mL centrifuge tube, and 45 μL of sample buffer at pH 6.5 (0.32 g of citric acid monohydrate and 2.45 g of disodium phosphate dodecahydrate are dissolved in 45 mL of ultra-pure water, and the volume is brought to 50 mL to prepare a citrate-phosphate buffer; 80 μL of 10% (w/v) sodium dodecyl sulfate solution is added to 200 μL of the buffer, the volume is brought to 1 mL with water, and the mixture is well mixed to give the sample buffer), 1 μL of internal standard (10 kDa protein, 5 mg/mL; Beckman Coulter, Catalog No. 390953) and 5 μL of 250 mmol/L NEM solution (62 mg of N-ethylmaleimide is dissolved in 2 mL of ultra-pure water) are added. The mixture is well mixed, heated at 70±2° C. for 10±2 min, cooled to room temperature, and transferred to a sample bottle for future use as a sample solution. The formulation buffer of the same volume as the sample is processed by the same method as above to prepare the blank solution. Conditions for sample injection: —5 kV for 20 s; separation voltage: —15 kV for 35 min. The capillary column temperature was controlled at 25° C. and the detection wavelength was 220 nm.

Charge Variants (CEX-HPLC)

The samples are measured with cation exchange chromatography (CEX-HPLC). The separation is performed using a MabPac SCX-10 strong cation exchange chromatographic column. The mobile phase A is a 10 mmol/L phosphate buffer (1.33 g of $NaH_2PO_4.12H_2O$ and 0.54 g of $Na_2HPO_4.12H_2O$ are dissolved in 800 mL of ultra-pure water, the volume is brought to 1000 mL, and the mixture is filtered through a Φ 0.22 μm filter membrane), and the mobile phase B is a 10 mmol/L phosphate+500 mmol/L sodium chloride buffer (1.33 g of $NaH_2PO_4.2H_2O$, 0.54 g of $Na_2HPO_4.12H_2O$ and 29.22 g of NaCl are dissolved in 800 mL of ultra-pure water, the volume is brought to 1000 mL, and the mixture is filtered through a Φ 0.22 μm filter membrane). The sample is diluted to 2.0 mg/mL with ultra-pure water as a sample solution. The formulation buffer is diluted in the same manner as described above to prepare a blank solution. The blank solution and the sample solution are separately injected into a liquid chromatograph in an amount of 50 μL for determination. The flow rate of the mobile phase is 1.0 mL/min, the collection time is 35 min, the column temperature is 35° C., the detection wavelength is 280 nm, and the temperature of the sample tray is 10° C. The sample solution is injected for analysis, and the contents of the principal component, the acidic component and the basic component are calculated by area normalization.

Charge Variants (iCIEF)

The determination is conducted by imaged capillary isoelectric focusing (iCIEF). The inner diameter of the capillary is 100 μm, and the total length is 5 cm. The capillary column is rinsed with 0.5% methylcellulose solution (hereinafter abbreviated as MC solution) and ultra-pure water before electrophoresis. The sample is injected in vacuum for 55 s, the pre-focusing is conducted at 1.5 kV for 1 min, the focusing is conducted at 3 kV for 8 min, the sample injection time is 55 s, the temperature of the sample tray is 10° C., the capillary column temperature is room temperature, and the detection wavelength is 280 nm. The cathodic stabilizer is 500 mmol/L arginine solution. 3 mol/L urea is added to improve the protein solubility, and 0.5% MC solution is added to decrease the adhesion between the protein and the capillary. The sample is diluted to 1 mg/mL with water, 20 μL of the diluted sample solution described above is added to 78 μL of a premixed solution, and the mixture is well mixed to prepare a test sample solution. The same procedures are performed using the formulation buffer to prepare a blank solution.

EXAMPLES

Example 1. Preparation and Purification of IL-23p19 Antibody

The antibody 17D1-YTE specifically binding to IL-23p19 was obtained as described in PCT Application No. PCT/CN2019/121261. The antibody has a heavy chain sequence of SEQ ID NO: 9 and a light chain sequence of SEQ ID NO: 10. PCT Application No. PCT/CN2019/121261 is incorporated herein by reference in its entirety. Briefly, the antibody was recombinantly expressed in CHO cells and purified by affinity chromatography to give the IL-23p19 antibody sample used in the pH screening test of the present invention, and purified by cation exchange chromatography to give the IL-23p19 antibody sample used in the formula screening test of the present invention.

Example 2. pH Screening Test 2.1. Procedures

This example examined the effect of citric acid buffer systems at pH 5.0, 5.5, 6.0 and 6.5 on the stability of the purified IL-23p19 antibody in Example 1 to give a superior pH range.

20 mM sodium citrate and 150 mM sodium chloride were prepared, and the pH of the solution was adjusted to 5.0, 5.5, 6.0 and 6.5 with hydrochloric acid. The purified IL-23p19 antibody in Example 1 was exchanged into buffers at the different pH values described above by ultrafiltration. The protein content was adjusted to 50 mg/mL The solution was filtered and aliquoted into vials, stoppered and capped. The sample described above was placed in a constant temperature and humidity chamber at 40±2° C., and sampling was performed at day 0, 1, 3, 5 and 10. The samples were cryopreserved in an ultra-low temperature freezer, then thawed and well mixed, and sent for analysis.

2.2 Results (1) Appearance and Visible Particles

The samples of the groups were clear to slightly opalescent, colorless to pale yellow liquids free of particles in appearance after storage at 40±2° C. for 10 days. That is, the samples of the groups are acceptable in terms of both appearance and visible particles.

(2) Protein Content

The results of the protein content assay are shown in Table 1. The results show that there were no significant changes in protein content (rate of change ≤10%) in the samples of the groups after storage at 40±2° C. for 10 days.

TABLE 1

Protein content results of the pH screening test (UV method, mg/mL)

| | | 40° C. ± 2° C. | | | |
|---|---|---|---|---|---|
| Sample name | Day 0 | Day 1 | Day 3 | Day 5 | Day 10 |
| pH 5.0 | 52.3 | 52.7 | 53.1 | 53.7 | 53.5 |
| pH 5.5 | 53.7 | 53.4 | 53.5 | 53.7 | 53.5 |
| pH 6.0 | 53.0 | 53.3 | 53.5 | 53.6 | 54.4 |
| pH 6.5 | 55.5 | 55.7 | 54.8 | 55.4 | 55.3 |

(3) Purity

Purity (SEC-HPLC): there were no significant changes in purity (change in purity ≤1%) in the samples of the groups after storage at 40±2° C. for 10 days. The results are shown in Table 2.

Purity (non-reduced CE-SDS): there were no significant changes in purity (change in purity ≤2%) in the samples of the groups after storage at 40±2° C. for 10 days. The results are shown in Table 3.

TABLE 2

Purity results of the pH screening test (SEC-HPLC, %)

| | | 40° C. ± 2° C. | | |
|---|---|---|---|---|
| Sample name | Day 0 | Day 3 | Day 5 | Day 10 |
| pH 5.0 | 99.2 | 99.0 | 98.9 | 98.7 |
| pH 5.5 | 99.2 | 99.1 | 99.0 | 98.9 |
| pH 6.0 | 99.2 | 99.0 | 99.0 | 99.0 |
| pH 6.5 | 99.1 | 98.9 | 99.0 | 98.9 |

TABLE 3

Purity results of the pH screening test (non-reduced CE-SDS, %)

| | | 40° C. ± 2° C. | | |
|---|---|---|---|---|
| Sample name | Day 0 | Day 3 | Day 5 | Day 10 |
| pH 5.0 | 98.0 | 97.7 | 97.6 | 97.2 |
| pH 5.5 | 98.0 | 97.9 | 97.7 | 97.5 |
| pH 6.0 | 98.1 | 98.1 | 97.7 | 97.6 |
| pH 6.5 | 98.0 | 98.0 | 97.6 | 97.7 |

(4) Charge Variants

Figure 2:
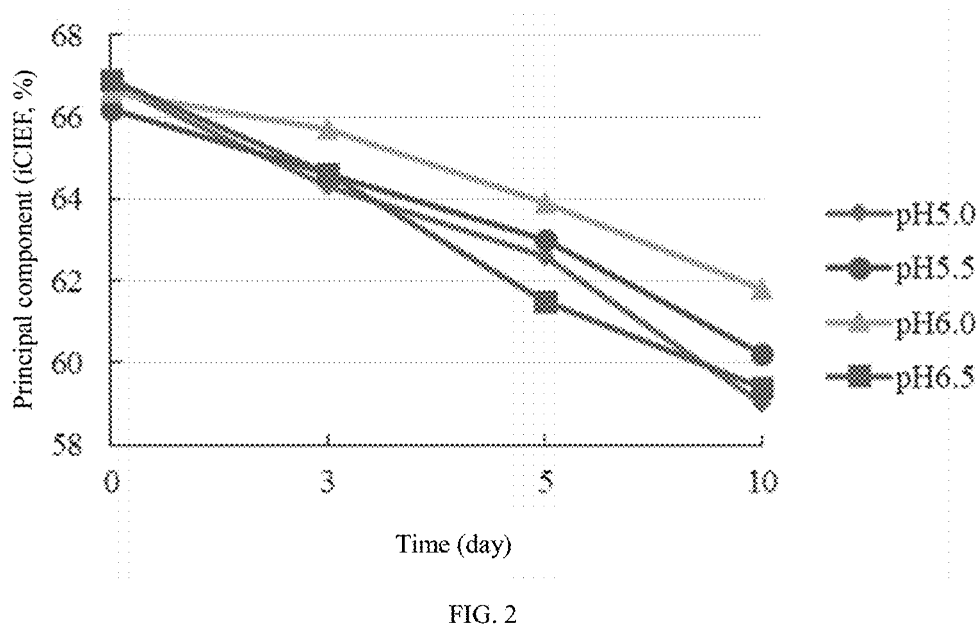
FIG. 2 a graph showing the change in charge variant-principal component in a pH screening test (iCIEF, 40±2° C.).

The results for charge variants (iCIEF) are shown in Table 4, and the trends of change are shown in FIGS. 1 and 2. The results show that the changes in charge variants in the samples of the groups are mainly manifested as an increase in the acidic component and a decrease in the principal component after storage at 40±2° C. for 10 days. The changes in the acidic components of the samples at pH 5.5-6.0 are 7.3%, 6.2%, 4.5% and 7.7%, respectively, which are small; the changes in the principal components of the samples at pH 5.5-6.0 are 7.8%, 6.0%, 4.8% and 7.5%, respectively, which are small.

TABLE 4

| Charge variant results of the pH screening test (iCIEF, %) | | | | | | | |
|---|---|---|---|---|---|---|---|
| | | | 40° C. ± 2° C. | | | Absolute change with |
| | Sample name | Day 0 | Day 3 | Day 5 | Day 10 | respect to day 0 (%) |
| pH 5.0 | Acidic component | 28.7 | 31.1 | 32.2 | 36.0 | 7.3 |
| | Principal component | 66.8 | 64.3 | 62.6 | 59.0 | 7.8 |
| | Basic component | 4.4 | 4.6 | 5.2 | 5.0 | 0.6 |
| pH 5.5 | Acidic component | 28.6 | 30.8 | 32.3 | 34.8 | 6.2 |
| | Principal component | 66.2 | 64.6 | 63.0 | 60.2 | 6.0 |
| | Basic component | 5.2 | 4.6 | 4.7 | 5.1 | 0.1 |
| pH 6.0 | Acidic component | 29.1 | 30.0 | 31.5 | 33.6 | 4.5 |
| | Principal component | 66.6 | 65.7 | 63.9 | 61.8 | 4.8 |
| | Basic component | 4.3 | 4.3 | 4.6 | 4.6 | 0.3 |
| pH 6.5 | Acidic component | 28.6 | 31.1 | 33.5 | 36.3 | 7.7 |
| | Principal component | 66.9 | 64.6 | 61.5 | 59.4 | 7.5 |
| | Basic component | 4.5 | 4.3 | 5.0 | 4.3 | 0.2 |

In summary, the pH screening test results show that a citric acid buffer system with a pH between 5.5 and 6.0 is suitable for the antibody formulation formula. A pH of about 6.0±0.3 was selected for the next formula determination test.

Example 3. Formula Determination Test

3.1. Procedures

According to the pH screening test results described above and experience of the formulation formula development platform, the effect of different stabilizers (sorbitol, sucrose and arginine) on the stability of the antibody protein was examined A total of 4 formulas were designed, and detailed information on formulas is shown in Table 5.

TABLE 5

| Information on formulas | |
|---|---|
| No. | Information on formula |
| Formula 1 | 1.55 mg/mL histidine, 80.00 mg/mL sucrose, 0.50 mg/mL polysorbate 80, pH 6.0 |
| Formula 2 | 1.55 mg/mL histidine, 50.00 mg/mL sorbitol, 0.50 mg/mL polysorbate 80, pH 6.0 |
| Formula 3 | 1.55 mg/mL histidine, 50.00 mg/mL sucrose, 0.50 mg/mL polysorbate 80, 13.94 mg/mL arginine, pH 6.0 |
| Formula 4 | 1.55 mg/mL histidine, 30.00 mg/mL sorbitol, 0.50 mg/mL polysorbate 80, 13.94 mg/mL arginine, pH 6.0 |

Buffers of each formula were prepared according to Table 5, the pH was adjusted to 6.0 with hydrochloric acid, and the antibody protein was exchanged into the corresponding formula solutions by ultrafiltration. The protein contents in each formula were adjusted to about 100 mg/mL after the exchange, and then the resulting solutions were aseptically aliquoted into 2R vials, which were then stoppered, capped, labelled, and subjected to accelerated experiments to obtain a better formulation formula. The experimental conditions and sampling schedule are shown in Table 6.

TABLE 6

| Experimental conditions and sampling schedule | | |
|---|---|---|
| No. | Experimental conditions | Experimental scheme and sampling time points |
| 1 | 40° C. ± 2° C. | Sampling at day 0, week 1, week 2 and month 1 |
| 2 | 25° C. ± 2° C. | Sampling at day 0, month 1, month 2 and month 3 |
| 3 | 5° C. ± 3° C. | Sampling at month 2 |

3.2. Results (1) Appearance and Visible Particles

The 4 formulas are acceptable in terms of appearance and visible particles under three different temperature experimental conditions.

(2) Protein Content

There were no significant changes in protein content (change rate ≤10%) in the 4 formulas at 40±2° C., 25±2° C. and 5±3° C. The results are shown in Table 7.

TABLE 7

| Protein content results of the formula screening test (UV method. mg/mL) | | | | | | | | |
|---|---|---|---|---|---|---|---|---|
| | | 40° C. ± 2° C. | | | 25° C. ± 2° C. | | | 5° C. ± 3° C. |
| Sample name | Day 0 | Week 1 | Week 2 | Month 1 | Month 1 | Month 2 | Month 3 | Month 2 |
| Formula 1 | 100.9 | 101.5 | 101.3 | 99.3 | 102.7 | 100.1 | 101.7 | 100.9 |
| Formula 2 | 102.9 | 103.7 | 103.1 | 100.3 | 100.5 | 102.5 | 102.1 | 102.9 |
| Formula 3 | 100.3 | 102.5 | 102.1 | 102.7 | 101.7 | 101.7 | 100.9 | 101.5 |
| Formula 4 | 102.5 | 102.3 | 102.5 | 100.9 | 101.9 | 102.1 | 101.5 | 101.9 |

(3) Purity

Purity (SEC-HPLC): there were no significant changes in purity (change in purity ≤1%) in formulas 1 to 4 at all the temperatures. The results are shown in Table 8.

Purity (non-reduced CE-SDS): there were no significant changes in purity (change in purity ≤2%) in formulas 1 to 3 at all the temperatures, and the change in concentration in the sample of formula 4 is greater than those of formulas 1 to 3 after accelerating at 25±2° C. for 3 months and storage at 5±3° C. for 2 months. The results are shown in Table 9.

TABLE 8

Purity results of the formula screening test (SEC-HPLC, %)

| | | 40° C. ± 2° C. | | | 25° C. ± 2° C. | | | 5° C. ± 3° C. |
|---|---|---|---|---|---|---|---|---|
| Sample name | Day 0 | Week 1 | Week 2 | Month 1 | Month 1 | Month 2 | Month 3 | Month 2 |
| Formula 1 | 99.7 | 99.3 | 99.2 | 98.8 | 99.3 | 99.2 | 99.0 | 99.5 |
| Formula 2 | 99.7 | 99.3 | 99.1 | 98.8 | 99.3 | 99.1 | 98.9 | 99.5 |
| Formula 3 | 99.7 | 99.4 | 99.3 | 99.0 | 99.4 | 99.3 | 99.1 | 99.6 |
| Formula 4 | 99.7 | 99.4 | 99.3 | 99.0 | 99.4 | 99.3 | 99.1 | 99.6 |

TABLE 9

Purity results of the formula screening test (non-reduced CE-SDS, %)

| | | 40° C. ± 2° C. | | | 25° C. ± 2° C. | | | 5° C. ± 3° C. |
|---|---|---|---|---|---|---|---|---|
| Sample name | Day 0 | Week 1 | Week 2 | Month 1 | Month 1 | Month 2 | Month 3 | Month 2 |
| Formula 1 | 98.8 | 98.7 | 98.5 | 98.1 | 98.8 | 97.4 | 96.9 | 98.2 |
| Formula 2 | 98.8 | 98.7 | 98.5 | 98.2 | 98.2 | 97.8 | 97.1 | 98.0 |
| Formula 3 | 98.9 | 98.6 | 98.6 | 98.2 | 98.7 | 97.5 | 97.0 | 98.0 |
| Formula 4 | 98.9 | 98.7 | 98.5 | 98.1 | 98.6 | 97.2 | 96.8 | 97.7 |

(4) Charge Variants

Figure 3:
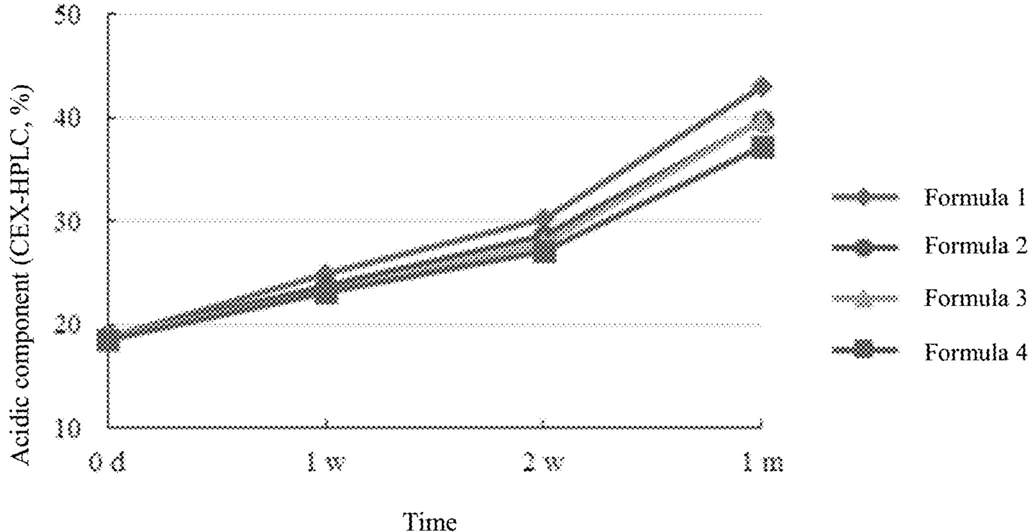
FIG. 3 is a graph showing the change in charge variant-acidic component in a formula determination test (CEX-HPLC, 40±2° C.).
Figure 4:
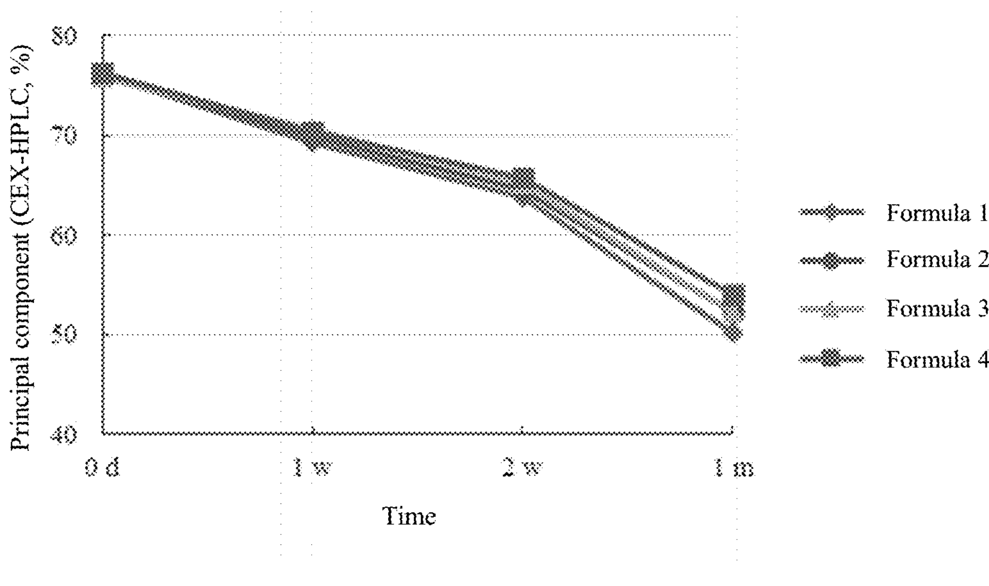
FIG. 4 is a graph showing the change in charge variant-principal component in a formula determination test (CEX-HPLC, 40±2° C.).

The results for charge variants (CEX-HPLC) are shown in Table 10, and the trends of change are shown in FIGS. 3 and 4. The results show that the changes in charge variants in the samples of the groups are mainly manifested as an increase in the acidic component and a decrease in the principal component at 40±2° C. The degrees of change in the acidic component (21%) and the principal component (23.8%) of formula 2 are less than those in the acidic component (24.3%) and the principal component (26.1%) of formula 1; the degrees of change in the acidic component (18.7%) and the principal component (22.3%) of formula 4 are less than those in the acidic component (20.8%) and the principal component (23.6%) of formula 3, indicating that sorbitol is better than sucrose as a stabilizer for the antibody disclosed herein. The charge variants changed after accelerating at 25±2° C. for 3 months, but there were no significant differences between formulas 1 and 2 and between formulas 3 and 4 (the differences between the formulas ≤2%). There were no significant changes in the charge variants (changes in principal component, acidic component and basic component ≤2%) in the 4 formulas after storage at 5±3° C. for 2 months.

TABLE 10

Charge variant results of the formula screening test (CEX-HPLC, %)

| | | | 40° C. ± 2° C. | | | | 25° C. ± 2° C. | | | | 5° C. ± 3° C. |
|---|---|---|---|---|---|---|---|---|---|---|---|
| | Groups | Day 0 | Week 1 | Week 2 | Month 1 | Change | Month 1 | Month 2 | Month 3 | Change | Month 2 |
| Formula 1 | Acidic component | 18.7 | 24.9 | 30.2 | 43 | 24.3 | 24.3 | 27.6 | 31.9 | 13.2 | 19.7 |
| | Principal component | 76.2 | 69.3 | 63.8 | 50.1 | 26.1 | 69.6 | 66.3 | 61.7 | 14.5 | 75.1 |
| | Basic component | 5.1 | 5.8 | 6 | 6.9 | 1.8 | 6.1 | 6.1 | 6.4 | 1.3 | 5.3 |
| Formula 2 | Acidic component | 18.8 | 23.7 | 28.7 | 39.8 | 21 | 23.6 | 26.7 | 30.1 | 11.3 | 19.7 |
| | Principal component | 76.1 | 69.9 | 64.6 | 52.3 | 23.8 | 69.9 | 66.4 | 62.6 | 13.5 | 74.9 |
| | Basic component | 5.2 | 6.4 | 6.7 | 7.9 | 2.7 | 6.5 | 6.8 | 7.3 | 2.1 | 5.4 |
| Formula 3 | Acidic component | 18.9 | 23.1 | 27.9 | 39.7 | 20.8 | 22.5 | 26 | 29.7 | 10.8 | 19.5 |
| | Principal component | 75.9 | 70.6 | 65.2 | 52.3 | 23.6 | 71 | 67 | 62.4 | 13.5 | 75.2 |
| | Basic component | 5.2 | 6.3 | 6.9 | 8 | 2.8 | 6.5 | 7 | 7.9 | 2.7 | 5.3 |
| Formula 4 | Acidic component | 18.6 | 23.1 | 27.1 | 37.3 | 18.7 | 22.8 | 26.2 | 29.5 | 10.9 | 19.7 |
| | Principal component | 76.3 | 70.3 | 65.8 | 54 | 22.3 | 70.1 | 66.3 | 62.3 | 14 | 74.7 |
| | Basic component | 5.1 | 6.6 | 7.2 | 8.7 | 3.6 | 7.1 | 7.5 | 8.2 | 3.1 | 5.6 |

Example 4. Process Verification Experiment

Based on the results of each experiment in Example 3, formula 2 was selected as the optimal formula. Meanwhile, given the stability and convenience requirements in the actual production process, a fixed ratio of histidine hydrochloride to histidine was selected to prepare the formula with a pH of 6.0±0.3—that is, the following formula was adopted: 100 mg/mL recombinant anti-interleukin 23p19 subunit antibody, 0.76 mg/mL histidine, 1.08 mg/mL histidine hydrochloride, 50.00 mg/mL sorbitol, 0.50 mg/mL polysorbate 80, pH 6.0±0.3.

Three batches of finished formulations were produced on a pilot scale, and the actual pH values were all pH 6.2. The long-term stability was investigated at 5±3° C., and sampling was performed at months 0, 3, 6, 9 and 12. The results are shown in Table 11. The results show that this formula gives good protein stability, and there were no significant differences between these batches. The formulations meet the quality criteria in the actual production process.

TABLE 11

Results of the process verification experiment

| Test items | Production quality criteria | Batch | Month 0 | Month 3 | Month 6 | Month 9 | Month 12 |
|---|---|---|---|---|---|---|---|
| Protein content | 90.0-110.0 mg/mL | 1 | 99.0 | 100.5 | 100.0 | 98.2 | 98.4 |
| UV method | Rate of change in | 2 | 99.3 | 101.6 | 101.2 | 98.9 | 99.5 |
| | protein content ≤10% | 3 | 100.3 | 102.4 | 102.2 | 100.0 | 98.4 |
| Purity | ≥95.0% | 1 | 99.6 | 99.5 | 99.5 | 99.4 | 99.4 |
| SEC-HPLC | | 2 | 99.7 | 99.6 | 99.5 | 99.5 | 99.4 |
| | | 3 | 99.7 | 99.6 | 99.5 | 99.4 | 99.4 |
| Purity Non- | ≥90.0% | 1 | 97.8 | 97.7 | 97.8 | 98.1 | 97.9 |
| reduced CE-SDS | | 2 | 98 | 97.9 | 98 | 98.1 | 98 |
| | | 3 | 98 | 97.8 | 97.8 | 98.1 | 98 |
| Charge variants | Principal component: | 1 | 78.2 | 78.5 | 77.5 | 76.5 | 76.3 |
| (CEX-HPLC) | should be ≥50.0% | 2 | 78.8 | 78.6 | 77.9 | 77 | 76.5 |
| | | 3 | 78.4 | 78.5 | 77.7 | 76.9 | 76.7 |
| | Acidic component | 1 | 15.7 | 15 | 15.8 | 16.2 | 17 |
| | | 2 | 15.5 | 15.1 | 15.9 | 16.3 | 17.1 |
| | | 3 | 15.8 | 15.1 | 15.8 | 16.3 | 16.9 |
| | Basic component | 1 | 6.2 | 6.5 | 6.7 | 7.2 | 6.7 |
| | | 2 | 5.7 | 6.3 | 6.2 | 6.7 | 6.4 |
| | | 3 | 5.8 | 6.4 | 6.5 | 6.8 | 6.4 |

The exemplary embodiments of the present invention have been described above. It should be understood by those skilled in the art that these contents are merely exemplary, and various other replacements, adaptations and modifications can be made within the scope of the present invention. Accordingly, the present invention is not limited to the specific embodiments listed herein.

The invention claimed is:

1. A liquid antibody formulation, comprising:

(i) an anti-IL-23p19 antibody;

(ii) a buffer, (iii) a stabilizer, and (iv) a surfactant, wherein the anti-IL-23p19 antibody comprises the following 6 CDRs:

a heavy chain VH CDR1 of (SEQ ID NO: 1) GYTFTSYLMH;

a heavy chain VH CDR2 of (SEQ ID NO: 2) YINPYNEGTN;

a heavy chain VH CDR3 of (SEQ ID NO: 3) NWDLPY;

a light chain VL CDR1 of (SEQ ID NO: 4) RASQSISDYLH;

a light chain VL CDR2 of (SEQ ID NO: 5) YASQSMS; and a light chain VL CDR3 of (SEQ ID NO: 6) QQGHSFPFT, and the boundaries of the CDRs are determined as per the AbM scheme.

2. The liquid antibody formulation according to claim 1, wherein the anti-IL-23p19 antibody in the liquid antibody formulation is at a concentration of about 25-250 mg/mL.

3. The liquid antibody formulation according to claim 2, wherein buffer is a histidine-histidine hydrochloride buffer, or a citric acid-sodium citrate buffer.

4. The liquid antibody formulation according to claim 3, wherein the buffer is selected from the group consisting of:

(i) histidine at about 0.775-3.1 mg/mL; and (ii) a combination of histidine and histidine hydrochloride with a histidine content of about 0.38-1.52 mg/mL and a histidine hydrochloride content of about 0.54-2.16 mg/mL.

5. The liquid antibody formulation according to claim 4, wherein the stabilizer is selected from the group consisting of:

(i) sorbitol at about 25-100 mg/mL;

(ii) sucrose at about 40-160 mg/mL;

(iii) a combination comprising sorbitol and arginine, wherein the sorbitol is at about 15-60 mg/mL, and the arginine is at about 6.97-27.88 mg/mL; and (iv) a combination comprising sucrose and arginine, wherein the sucrose is at about 25-100 mg/mL, and the arginine is at about 6.97-27.88 mg/mL.

6. The liquid antibody formulation according to claim 5, wherein the surfactant in the liquid antibody formulation is selected from the group consisting of: a polysorbate surfactant, poloxamer, polyethylene glycol and combinations thereof.

7. The liquid antibody formulation according to claim 6, wherein the surfactant is at a concentration of about 0.1-1 mg/mL.

8. The liquid antibody formulation according to claim 1, wherein the anti-IL-23p19 antibody comprises a heavy chain variable region VH and a light chain variable region VL, wherein the heavy chain variable region comprises a sequence of SEQ ID NO: 7 or a sequence having at least 90% identity thereto, and the light chain variable region comprises a sequence of SEQ ID NO: 8 or a sequence having at least 90% identity thereto.

9. The liquid antibody formulation according to claim 8, wherein the anti-IL-23p19 antibody is an IgG1 antibody, and wherein the anti-IL-23p19 antibody comprises a heavy chain sequence of SEQ ID NO: 9 or a sequence having at least 90% identity thereto, and a light chain sequence of SEQ ID NO: 10 or a sequence having at least 90% identity thereto.

10. The liquid antibody formulation according to claim 1, wherein the anti-IL-23p19 antibody is recombinantly expressed in HEK293 cells or CHO cells.

11. The liquid antibody formulation according to claim 1, wherein the liquid formulation is an injection formulation, or an infusion formulation.

12. The liquid antibody formulation according to claim 1, wherein the liquid antibody formulation comprises:

(i) the anti-IL-23p19 antibody at about 50-200 mg/mL;
(ii) histidine at about 0.775-3.1 mg/mL;
(iii) sorbitol at about 40-60 mg/mL; and
(iv) polysorbate 80 at about 0.2-0.8 mg/mL;
wherein the liquid formulation has a pH of 6.0+0.3;
or wherein the liquid antibody formulation comprises:
(i) the anti-IL-23p19 antibody at about 50-200 mg/mL;
(ii) histidine at about 0.775-3.1 mg/mL;
(iii) sorbitol at about 20-40 mg/mL, and arginine at about 10.45-17.42 mg/mL; and
(iv) polysorbate 80 at about 0.2-0.8 mg/mL;
wherein the liquid formulation has a pH of 6.0+0.3;
or wherein the liquid antibody formulation comprises:
(i) the anti-IL-23p19 antibody at about 50-200 mg/mL;
(ii) a histidine buffer at about 0.775-3.1 mg/mL;
(iii) sucrose at about 70-90 mg/mL; and
(iv) polysorbate 80 at about 0.2-0.8 mg/mL;
wherein the liquid formulation has a pH of 6.0+0.3;
or wherein the liquid antibody formulation comprises:
(i) the anti-IL-23p19 antibody at about 50-200 mg/mL;
(ii) histidine at about 0.775-3.1 mg/mL;
(iii) sucrose at about 40-60 mg/mL, and arginine at about 10.45-17.42 mg/mL; and
(iv) polysorbate 80 at about 0.2-0.8 mg/mL;
wherein the liquid formulation has a pH of 6.0+0.3;
or wherein the liquid antibody formulation comprises:
(i) the anti-IL-23p19 antibody at about 50-200 mg/mL;
(ii) histidine at about 0.38-1.52 mg/mL, and histidine hydrochloride at about 0.54-2.16 mg/mL;
(iii) sorbitol at about 40-60 mg/mL; and
(iv) polysorbate 80 at about 0.2-0.8 mg/mL;
wherein the liquid formulation has a pH of 6.0+0.3;
or wherein the liquid antibody formulation comprises:
(i) the anti-IL-23p19 antibody at about 50-200 mg/mL;
(ii) histidine at about 0.38-1.52 mg/mL, and histidine hydrochloride at about 0.54-2.16 mg/mL;
(iii) sorbitol at about 20-40 mg/mL, and arginine at about 10.45-17.42 mg/mL; and
(iv) polysorbate 80 at about 0.2-0.8 mg/mL;
wherein the liquid formulation has a pH of 6.0+0.3;
or wherein the liquid antibody formulation comprises:
(i) the anti-IL-23p19 antibody at about 50-200 mg/mL;
(ii) histidine at about 0.38-1.52 mg/mL, and histidine hydrochloride at about 0.54-2.16 mg/mL;
(iii) sucrose at about 70-90 mg/mL; and
(iv) polysorbate 80 at about 0.2-0.8 mg/mL;
wherein the liquid formulation has a pH of 6.0+0.3;
or wherein the liquid antibody formulation comprises:
(i) the anti-IL-23p19 antibody at about 50-200 mg/mL;
(ii) histidine at about 0.38-1.52 mg/mL, and histidine hydrochloride at about 0.54-2.16 mg/mL;
(iii) sucrose at about 40-60 mg/mL, and arginine at about 10.45-17.42 mg/mL; and
(iv) polysorbate 80 at about 0.2-0.8 mg/mL;
wherein the liquid formulation has a pH of 6.0+0.3.

13. A solid antibody formulation, obtained by solidifying the liquid antibody formulation according to claim 1.

14. A delivery device, comprising the liquid antibody formulation according to claim 1.

15. A pre-filled syringe, comprising the liquid antibody formulation according to claim 1.

16. A method for treating an autoimmune disease that expresses an elevated level of IL-23 the method comprising administering the liquid antibody formulation according to claim 1 to a subject.

17. A delivery device, comprising the solid antibody formulation according to claim 13.

18. A pre-filled syringe, comprising the solid antibody formulation according to claim 13.

19. A method for treating an autoimmune disease that expresses an elevated level of IL-23 the method comprising administering the solid antibody formulation according to claim 13 to a subject.

20. The method of claim 16, wherein the autoimmune disease is psoriasis, Crohn's disease, rheumatoid arthritis, ankylosing spondylitis, or psoriatic arthritis.

21. The liquid antibody formulation according to claim 1, wherein the liquid antibody formulation has a pH of about 5.2-6.3.

22. The liquid antibody formulation according to claim 1, wherein the liquid antibody formulation has a pH of about 6.0+0.3.

23. The liquid antibody formulation according to claim 3, wherein the buffer comprises histidine, histidine hydrochloride, or a combination thereof.

* * * * *

SEQUENCE LISTING

```
<160> NUMBER OF SEQ ID NOS: 10

<210> SEQ ID NO 1
<211> LENGTH: 10
<212> TYPE: PRT
<213> ORGANISM: Artificial Sequence
<220> FEATURE:
<223> OTHER INFORMATION: VH CDR1

<400> SEQUENCE: 1

Gly Tyr Thr Phe Thr Ser Tyr Leu Met His
1               5                   10


<210> SEQ ID NO 2
<211> LENGTH: 10
<212> TYPE: PRT
<213> ORGANISM: Artificial Sequence
<220> FEATURE:
<223> OTHER INFORMATION: VH CDR2

<400> SEQUENCE: 2

Tyr Ile Asn Pro Tyr Asn Glu Gly Thr Asn
1               5                   10
```

<210> SEQ ID NO 3
<211> LENGTH: 6
<212> TYPE: PRT
<213> ORGANISM: Artificial Sequence
<220> FEATURE:
<223> OTHER INFORMATION: VH CDR3

<400> SEQUENCE: 3

```
Asn Trp Asp Leu Pro Tyr
1               5
```

<210> SEQ ID NO 4
<211> LENGTH: 11
<212> TYPE: PRT
<213> ORGANISM: Artificial Sequence
<220> FEATURE:
<223> OTHER INFORMATION: VL CDR1

<400> SEQUENCE: 4

```
Arg Ala Ser Gln Ser Ile Ser Asp Tyr Leu His
1               5                   10
```

<210> SEQ ID NO 5
<211> LENGTH: 7
<212> TYPE: PRT
<213> ORGANISM: Artificial Sequence
<220> FEATURE:
<223> OTHER INFORMATION: VL CDR2

<400> SEQUENCE: 5

```
Tyr Ala Ser Gln Ser Met Ser
1               5
```

<210> SEQ ID NO 6
<211> LENGTH: 9
<212> TYPE: PRT
<213> ORGANISM: Artificial Sequence
<220> FEATURE:
<223> OTHER INFORMATION: VL CDR3

<400> SEQUENCE: 6

```
Gln Gln Gly His Ser Phe Pro Phe Thr
1               5
```

<210> SEQ ID NO 7
<211> LENGTH: 115
<212> TYPE: PRT
<213> ORGANISM: Artificial Sequence
<220> FEATURE:
<223> OTHER INFORMATION: VH

<400> SEQUENCE: 7

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Leu Met His Trp Val Arg Gln Ala Pro Gly Gln Gly Leu Glu Trp Met
        35                  40                  45

Gly Tyr Ile Asn Pro Tyr Asn Glu Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
```

```
                85                  90                  95

Ala Arg Asn Trp Asp Leu Pro Tyr Trp Gly Gln Gly Thr Leu Val Thr
            100                 105                 110

Val Ser Ser
        115


<210> SEQ ID NO 8
<211> LENGTH: 107
<212> TYPE: PRT
<213> ORGANISM: Artificial Sequence
<220> FEATURE:
<223> OTHER INFORMATION: VL

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asp Tyr
            20                  25                  30

Leu His Trp Tyr Gln Gln Lys Pro Gly Lys Ala Pro Lys Leu Leu Ile
        35                  40                  45

Lys Tyr Ala Ser Gln Ser Met Ser Gly Val Pro Ser Arg Phe Ser Gly
    50                  55                  60

Ser Gly Ser Gly Ser Asp Phe Thr Leu Thr Ile Ser Ser Leu Gln Pro
65                  70                  75                  80

Glu Asp Phe Ala Thr Tyr Tyr Cys Gln Gln Gly His Ser Phe Pro Phe
                85                  90                  95

Thr Phe Gly Gln Gly Thr Lys Leu Glu Ile Lys
            100                 105


<210> SEQ ID NO 9
<211> LENGTH: 444
<212> TYPE: PRT
<213> ORGANISM: Artificial Sequence
<220> FEATURE:
<223> OTHER INFORMATION: HC

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Leu Met His Trp Val Arg Gln Ala Pro Gly Gln Gly Leu Glu Trp Met
        35                  40                  45

Gly Tyr Ile Asn Pro Tyr Asn Glu Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asn Trp Asp Leu Pro Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160
```

```
Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Tyr Ile Thr Arg Glu Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440


<210> SEQ ID NO 10
<211> LENGTH: 214
<212> TYPE: PRT
<213> ORGANISM: Artificial Sequence
<220> FEATURE:
<223> OTHER INFORMATION: LC

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asp Tyr
            20                  25                  30

Leu His Trp Tyr Gln Gln Lys Pro Gly Lys Ala Pro Lys Leu Leu Ile
        35                  40                  45

Lys Tyr Ala Ser Gln Ser Met Ser Gly Val Pro Ser Arg Phe Ser Gly
    50                  55                  60

Ser Gly Ser Gly Ser Asp Phe Thr Leu Thr Ile Ser Ser Leu Gln Pro
65                  70                  75                  80
```

-continued

```
Glu Asp Phe Ala Thr Tyr Tyr Cys Gln Gln Gly His Ser Phe Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```